US009005909B2

(12) United States Patent
Markovtsov et al.

(10) Patent No.: US 9,005,909 B2
(45) Date of Patent: Apr. 14, 2015

(54) WHOLE BLOOD ASSAY FOR MEASURING AMPK ACTIVATION

(75) Inventors: Vadim Markovtsov, South San Francisco, CA (US); Yasumichi Hitoshi, Brisbane, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 455 days.

(21) Appl. No.: 13/333,817

(22) Filed: Dec. 21, 2011

(65) Prior Publication Data

US 2012/0178098 A1 Jul. 12, 2012

Related U.S. Application Data

(60) Provisional application No. 61/430,472, filed on Jan. 6, 2011.

(51) Int. Cl.
*G01N 33/573* (2006.01)
*G01N 33/49* (2006.01)
*G01N 33/53* (2006.01)

(52) U.S. Cl.
CPC .......... *G01N 33/573* (2013.01); *G01N 33/4915* (2013.01); *G01N 33/53* (2013.01); *G01N 33/49* (2013.01); *G01N 2333/91205* (2013.01); *G01N 2800/02* (2013.01)

(58) Field of Classification Search
USPC ....................................................... 435/7.23
See application file for complete search history.

(56) References Cited

U.S. PATENT DOCUMENTS 7,939,278 B2 * 5/2011 Perez et al. ................... 435/7.21
2009/0269773 A1 * 10/2009 Fantl et al. ........................ 435/6

OTHER PUBLICATIONS

Campas et al. (Acadesine activates AMPK and induces apoptosis in B-cell chronic lymphocytic leukemia cells but not in T lymphocyte, Blood 101 (9): 3674-3680 (2003).*
Aschenbach et al. 5' Adenosine Monophosphate-Activated Protein Kinase, Metabolism, and Exercise, Sports Med 34 (2): 91-103 (2004).*
PCT/US2011/066946, International Search Report and Written Opinion, dated Mar. 26, 2012, 9pgs.
Campas, et al., "Acadesine activates AMPK and induces apoptosis in B-cell chronic lymphocytic leukemia cells but not in T lymphocytes", Blood, 2003, 101:3674-80.
Rivera, et al., "Long-term resveratrol administration reduces metabolic disturbances and lowers blood pressure in obese Zucker rats", Biochem Pharmacol, 2009, 77:1053-63.
Towler, et al., "Amp-activated protein kinase in metabolic control and insulin signaling", Circulation, 2007, 100:328-48.
Catusse, et al., "Role of the atypical chemoattractant receptor CRAM in regulating CCL19 induced CCR7 responses in B-cell chronic lymphocytic leukemia", Mol Cancer, 2010 9:297.

(Continued)

*Primary Examiner* — Gail R Gabel
(74) *Attorney, Agent, or Firm* — James S. Keddie; Bozicevic, Field & Francis, LLP

(57) ABSTRACT

A method of sample analysis is provided. In certain embodiments, the method comprises: a) labeling cells of a blood sample using an antibody that specifically binds to phospho-AMPK or a phosphorylated target thereof, to produce a labeled sample; and b) measuring antibody binding by a population of blood cells of the labeled sample using flow cytometry. In particular embodiments, the method may further comprise, prior to the labeling step: contacting blood with a test agent ex vivo or in vivo; and comparing the evaluation to results obtained from a reference sample of blood cells.

16 Claims, 22 Drawing Sheets

(56) References Cited

OTHER PUBLICATIONS

Chen, et al., "Role of erythropoietin receptor signaling in parvovirus B19 replication in human erythroid progenitor cells", J Virol, 2010 84:12385.

Dong, et al., "Selective inhibition of PDGFR by imatinib elicits the sustained activation of ERK and downstream receptor signaling in malignant glioma cells", Int J Oncol, 2011 38:555.

Hinke, et al., "Methyl succinate antagonises biguanide-induced AMPK-activation and death of pancreatic beta-cells through restoration of mitochondrial electron transfer", Br J Pharmacol, 2007 150:1031.

Kefas, et al., "AICA-riboside induces apoptosis of pancreatic beta cells through stimulation of AMP-activated protein kinase", Diabetologica, 2003 46:250.

Kodiha, et al., "Localization of AMP kinase is regulated by stress, cell density, and signaling through the MEK—>ERK1/2 pathway", Am J Physiol Cell Physiol, 2007 293:C1427.

Saha, et al., "Downregulation of AMPK accompanies leucine- and glucose-induced increases in protein synthesis and insulin resistance in rat skeletal muscle", Diabetes. 2010 59:2426.

Sasaki, et al., "Metformin prevents progression of heart failure in dogs: role of AMP-activated protein kinase", Circulation, 2009 119:2568.

* cited by examiner

| Gender | Donor | pAMPK EC50, uM | | | | pACC EC50, uM | | | |
|---|---|---|---|---|---|---|---|---|---|
| | | Lymphocytes | | Granulocytes | | Lymphocytes | | Granulocytes | |
| | | Cmpd1 | Cmpd2 | Cmpd1 | Cmpd2 | Cmpd1 | Cmpd2 | Cmpd1 | Cmpd2 |
| Female | Donor 1 | 0.01 | 0.348 | 0.003 | 0.19 | 0.015 | 0.244 | NA | NA |
| Female | Donor 2 | 0.042 | 0.346 | 0.026 | 0.202 | 0.049 | 0.245 | NA | NA |
| Female | Donor 5 | 0.033 | 0.422 | 0.03 | 0.314 | 0.029 | 0.459 | NA | NA |
| Male | Donor 3 | 0.038 | 0.466 | 0.032 | 0.337 | 0.023 | 0.777 | NA | NA |
| Male | Donor 4 | 0.022 | 0.411 | 0.017 | 0.3 | 0.045 | 0.462 | NA | NA |
| Male | Donor 6 | 0.034 | 0.396 | 0.034 | 0.315 | 0.038 | 0.437 | NA | NA |
| Average | | 0.030 | 0.398 | 0.024 | 0.276 | 0.033 | 0.437 | NA | NA |
| St error | | 0.005 | 0.021 | 0.005 | 0.028 | 0.006 | 0.087 | NA | NA |
| Average female | | 0.028 | 0.372 | 0.020 | 0.235 | 0.031 | 0.316 | NA | NA |
| Average male | | 0.031 | 0.424 | 0.028 | 0.317 | 0.035 | 0.559 | NA | NA |

FIG. 8A

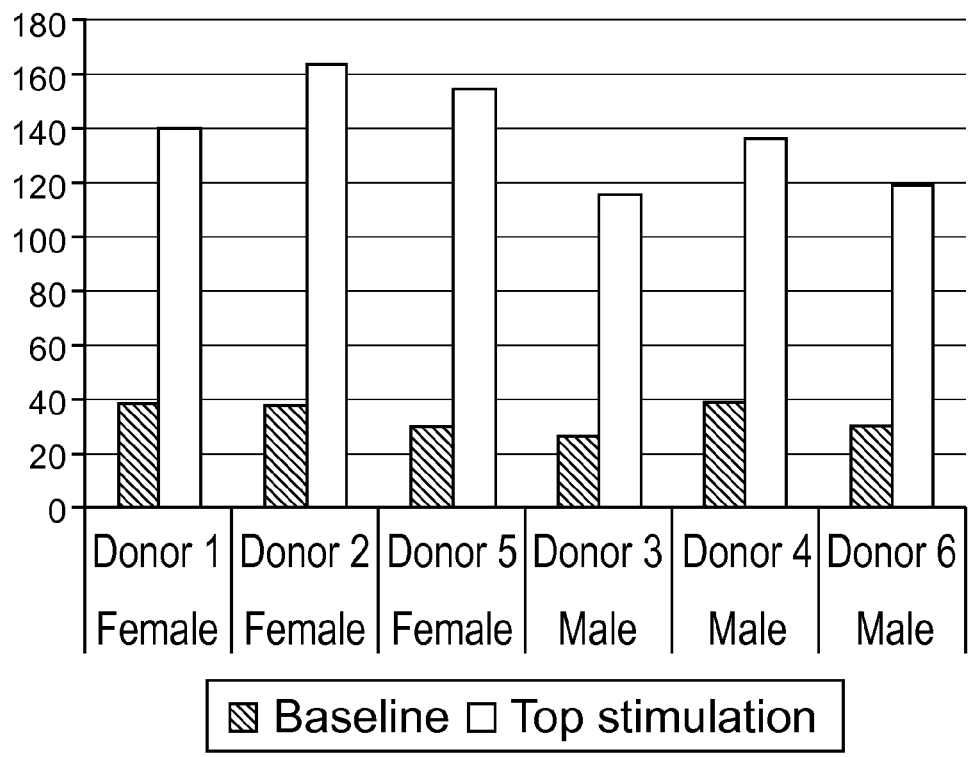
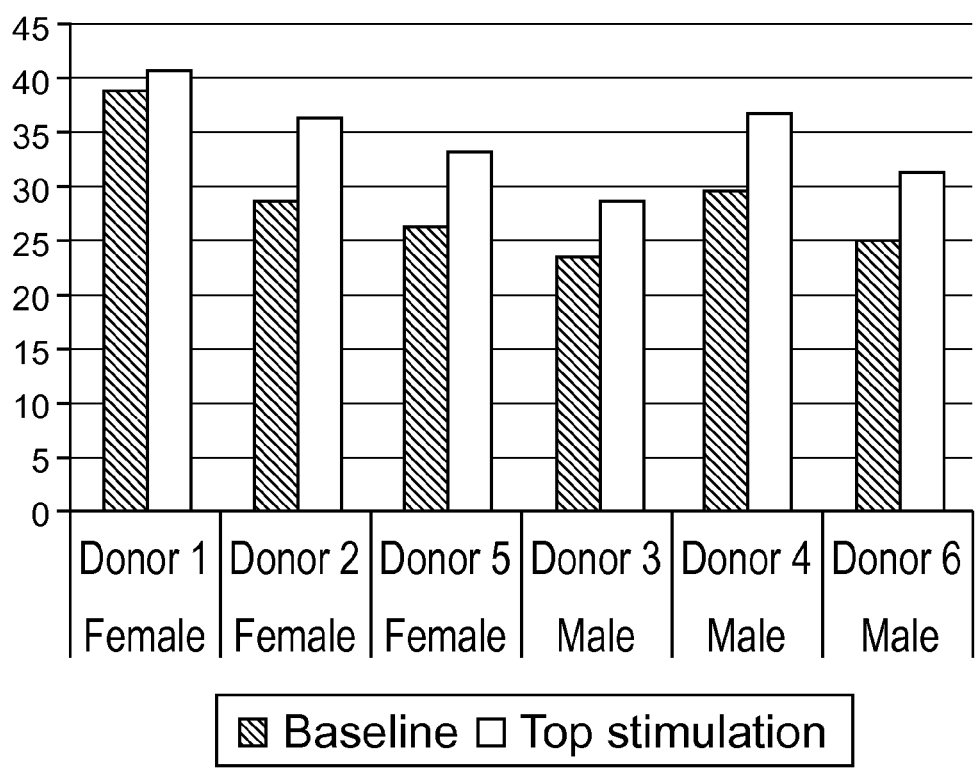
FIG. 8C

WHOLE BLOOD ASSAY FOR MEASURING AMPK ACTIVATION

CROSS REFERENCE TO RELATED APPLICATIONS

Pursuant to 35 U.S.C. §119(e), this application claims priority to the filing date of U.S. Provisional Patent Application Ser. No. 61/430,472 filed Jan. 6, 2011, the disclosure of which application is herein incorporated by reference.

BACKGROUND

AMPK (adenosine monophosphate kinase) is a heterotrimeric, multisubstrate kinase composed of one catalytic ($\alpha 1$ or $\alpha 2$), one regulatory ($\beta 1$ or $\beta 2$), and one AMP/ATP binding ($\gamma 1$, $\gamma 2$, or $\gamma 3$) subunit. The C terminus of the $\beta$ subunit interacts with both $\alpha$ and $\gamma$ subunits, and current evidence indicates that the $\beta$ subunit is an obligatory component of the active AMPK complex. The exact mechanism by which AMPK is regulated by the energy status of a cell is not fully understood. It is thought that when intracellular energy levels drop (i.e., when there is a low ATP:AMP ratio), AMP displaces ATP from the $\gamma$ subunit, causing a conformational change that allows upstream kinases (e.g., LKB1 or CaMKK$\beta$) to phosphorylate and activate the $\alpha$ subunit. Alternatively, AMPK may be constitutively phosphorylated, but is quickly dephosphorylated under normal conditions. At high AMP levels, however, AMP binding leads to a conformational change shielding activation site from such action by phosphatase.

AMPK acts as a sensor of energy status within cells and can be considered a master switch of energy metabolism because, upon activation, the enzyme phosphorylates a number of downstream protein substrates that have an effect on lipid biosynthesis, fatty acid oxidation, glucose uptake, gluconeogenesis and lipogenesis, for example. Phosphorylation of downstream targets by AMPK decreases ATP usage by the cell which, in turn, increases the ATP:AMP ratio in the cell which, in turn, decreases AMPK activity.

All those properties combine to make AMPK an attractive target in the treatment of diabetes, obesity and a variety of other metabolic disorders.

SUMMARY

A method of sample analysis is provided. In certain embodiments, the method comprises: a) labeling cells of a blood sample using an antibody that specifically binds to phospho-AMPK or a phosphorylated target thereof, to produce a labeled sample; and b) measuring antibody binding by a population of blood cells of the labeled sample using flow cytometry. In particular embodiments, the method may further comprise, prior to the labeling step: contacting blood with a test agent ex vivo or in vivo; and comparing the evaluation to results obtained from a reference sample of blood cells.

Without wishing to be bound to any scientific theory, it is believed that: a) the effect of an AMPK-modulatory compound or lifestyle (e.g., diet or exercise) that modulates AMPK can be determined by analyzing an organism's blood, and b) blood, which is a tissue that is not generally associated with energy production or use, can act as a surrogate for tissues that are associated with energy production or use (e.g., liver and muscle, etc.). Thus, the energy status of an organism can be evaluated using the organism's blood by flow cytometry using an antibody that specifically binds to phospho-AMPK or a phosphorylated target thereof. These methods do not require an invasive procedure (e.g., a tissue biopsy) and are faster and more economical compared to prior approaches (e.g., western blotting).

BRIEF DESCRIPTION OF THE DRAWINGS

Certain aspects of some embodiments of the invention may be best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIGS. 8A-8C. FIG. 8A is a table showing that there is low donor to donor variability in pAMPK and pACC stimulation using two AMPK activators. FIGS. 8B and 8C present graphs showing an analysis of the data presented in the table of FIG. 8A.

FIG. 17A shows an experimental plan whereas

DEFINITIONS

Figure 1:
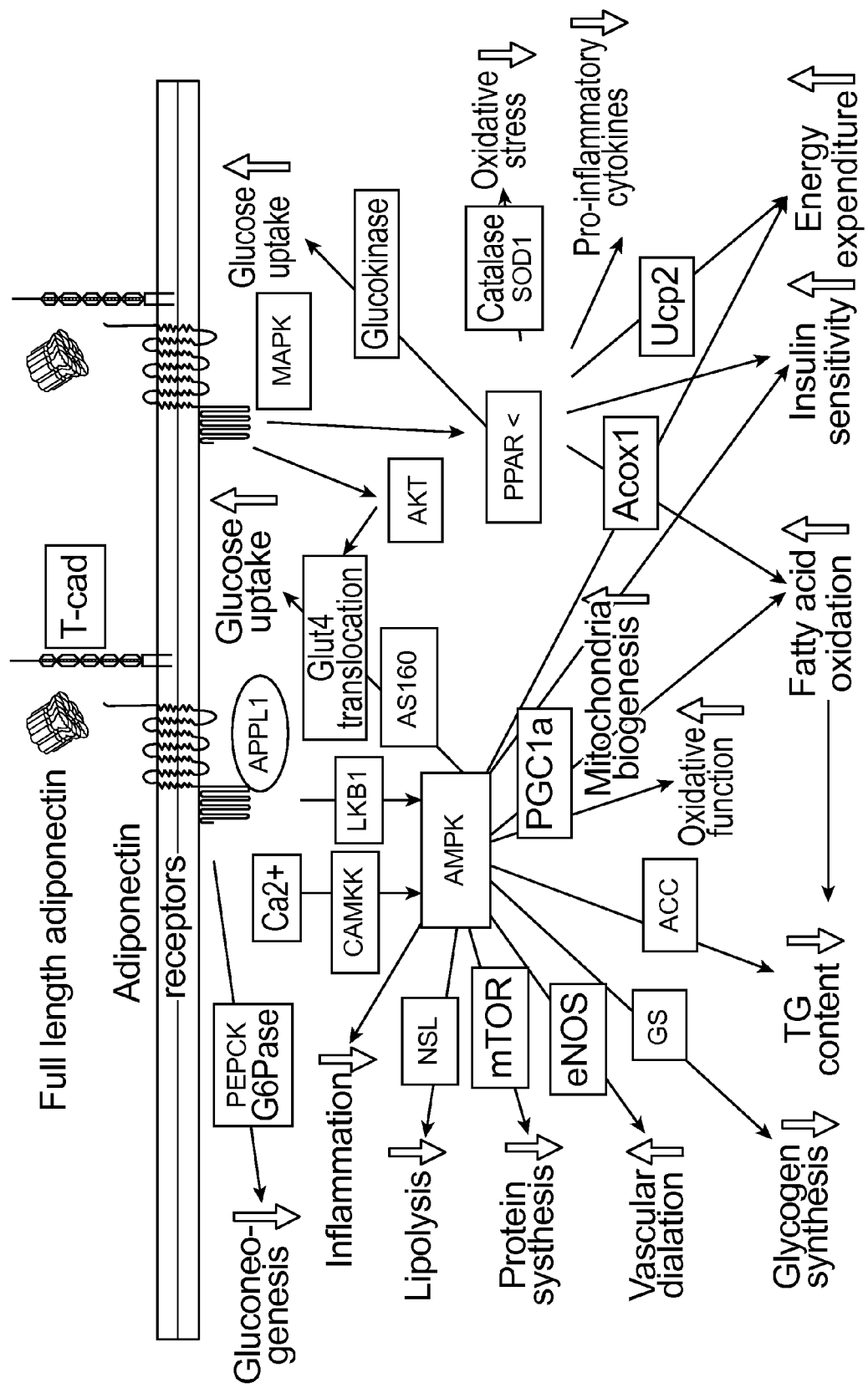
FIG. 1 schematically illustrates the AMPK pathway.

The term "biological sample" as used herein refers to any sample that contains or is made from living material. A biological sample may contain intact cells obtained from a multicellular organism. A biological sample may isolated from an individual, e.g., from a soft tissue or from a bodily fluid, or from a cell culture that is grown in vitro. A biological sample may be made from a soft tissue such as brain, adrenal gland, skin, lung, spleen, kidney, liver, spleen, lymph node, bone marrow, bladder stomach, small intestine, large intestine or muscle, etc. Bodily fluids include blood, plasma, saliva, mucous, phlegm, cerebral spinal fluid, pleural fluid, tears, lactal duct fluid, lymph, sputum, cerebrospinal fluid, synovial fluid, urine, amniotic fluid, and semen, etc. Biological samples also include cells grown in culture in vitro.

The term "intact cells" includes cells that have been fixed and/or permeabilized. Cells that have been lysed and/or sectioned or not intact cells. Western blots and assays in which either the proteins of a cell lysate or an antibody are affixed to a solid support (e.g., ELISAs) do not involve intact cells.

The term "blood sample" or grammatical equivalents thereof refer to a sample of whole blood or a sub-population of cells in whole blood. Sub-populations of cells in whole blood include platelets, red blood cells (erythrocytes), platelets and white blood cells (i.e., peripheral blood leukocytes, which are made up of neutrophils, lymphocites, eosinophils, basophils and monocytes). These five types of while blood cells can be further divided into two groups, granulocytes (which are also known as polymorphonuclear leukeocytes and include neutrophils, eosinophils and basophils) and mononuclear leukocytes (which include monocytes and lymphocytes). Lymphocytes can be further divided into T cells, B cells and NK cells. Peripheral blood cells are found in the circulating pool of blood and not sequestered within the lymphatic system, spleen, liver, or bone marrow. If blood is first contacted with an agent and then a sample of the blood is used in an assay, then a portion or all of the contacted blood may be used in the assay.

The term "capture agent" refers to an agent that binds a target molecule through an interaction that is sufficient to permit the agent to bind and concentrate the target molecule from a homogeneous mixture of different molecules. The binding interaction is typically mediated by an affinity region of the capture agent. Typical capture agents include any moiety that can specifically bind to a target molecule. In certain embodiments, a polypeptide, e.g., an antibody, may be employed.

The term "antibody" is used herein to refer to a capture agent that has at least an epitope binding domain of an antibody. Types of antibodies include monoclonal antibodies and antigen-binding fragments thereof (e.g., Fab, Fv, scFv, and Fd fragments, chimeric antibodies, humanized antibodies, single-chain antibodies, etc.) are known and need not be described in any further detail.

Capture agents "specifically bind" a target molecule. Accordingly, the term "capture agent" refers to a molecule or a multi-molecular complex which can specifically bind a target molecule, e.g., a phosphorylated polypeptide, with a dissociation constant ($K_D$) of less than about $10^{-6}$ M (e.g., less than about $10^{-7}$M, less than about $10^{-8}$M, less than about $10^{-9}$M, less than about $10^{-10}$ M, less than about $10^{-11}$ M, less than about $10^{-12}$ M, to as low as $10^{-16}$ M) without significantly binding to other molecules. The term "specific binding" refers to the ability of a capture agent to preferentially bind to a particular target molecule that is present in a homogeneous mixture of different target molecule. A specific binding interaction will discriminate between desirable (e.g., phosphorylated) and undesirable (e.g., unphosphorylated) target molecules in a sample, typically more than about 10 to 100-fold or more (e.g., more than about 1000- or 10,000-fold).

As used herein, the term "flow cytometry" refers to a method by which the individual cells of a sample are analyzed by their optical properties (e.g., light absorbance, light scattering and fluorescence properties, etc.) as they pass in a narrow stream in single file through a laser beam. Flow cytometry methods include fluorescence activated cell sorting (FACS) methods by which a population of cells having particular optical properties are separated from other cells.

As used herein, the term "labeling" includes direct and indirect labeling. An antibody may be fluorescently labeled with a fluorophore or a quantum dot, many of which are known.

The term "pre-determined" refers to an element whose identity is known prior to its use. An element may be known by name, sequence, molecular weight, its function, an amount, optical properties, or any other attribute or identifier.

The term "mixture", as used herein, refers to a combination of elements, e.g., cells, that are interspersed and not in any particular order. A mixture is homogeneous and not spatially separated into its different constituents. Examples of mixtures of elements include a number of different cells that are present in the same aqueous solution in a spatially undressed manner.

"Isolated" or "purified" refers to isolation of a substance (compound, polynucleotide, protein, polypeptide, polypeptide composition) such that the substance comprises a significant percent (e.g., greater than 2%, greater than 5%, greater than 10%, greater than 20%, greater than 50%, or more, usually up to about 90%-100%) of the sample in which it resides. A substantially purified component comprises at least 50%, 80%-85%, or 90-95% of the sample.

The term "assessing" includes any form of measurement, and includes determining if an element is present or not. The terms "determining", "measuring", "evaluating", "assessing" and "assaying" are used interchangeably and may include quantitative and/or qualitative determinations. Assessing may be relative or absolute. "Assessing the presence of" includes determining the amount of something present, and/or determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

As used herein, the term "geometric mean" refers to the mean of n numbers expressed as the n-th root of their product.

As used herein, the term "in vivo" refers to the body of a whole living organism, e.g., a living mammal As used herein, the term "ex vivo" refers to living tissue that has been removed from the body of a whole living organism, e.g., a living mammal A sample of blood that has been drawn from a mammal and contains living cells is an example of an ex vivo sample.

As used herein, the term "in vitro" refers to cells that have been grown in culture.

As used herein, the term "AMPK" or "AMP-activated protein kinase" refers to a heterotrimeric kinase composed of an alpha catalytic subunit, and non-catalytic beta and gamma subunits. AMPK is an important energy-sensing enzyme that monitors cellular energy status. In response to cellular metabolic stresses, AMPK is activated and phosphorylates and inactivates acetyl-CoA carboxylase (ACC) and beta-hydroxy beta-methylglutaryl-CoA reductase (HMGCR), key enzymes involved in regulating de novo biosynthesis of fatty acid and cholesterol, as well as other proteins involved in metabolism. AMPK and its role as an energy sensor has been reviewed in a variety of publications, including: Kemp et al (Trends Biochem. Sci. 1999 24:22-5), Hardie et al (Bioessays. 2001 23:1112-9), Musi et al (Curr. Drug Targets Immune Endocr. Metabol. Disord. 2002 2:119-27), Musi et al (Biochem. Soc. Trans. 2003 31:191-5) and Hardie (Endocrinology. 2003 144: 5179-83) and Aschenbach (Sports Med. 2004 34:91-103), which publications are incorporated by reference.

As used herein, the term "phospho-AMPK" or "p-AMPK" refers to a form of AMPK in which the α subunit has a phosphorylated threonine at position 172. Phosphorylation at this position is done by an upstream AMKP kinase (AMPKK). Phosphorylation at this position causes the kinase to phosphorylate downstream targets. One downstream target of phospho-AMPK is ACC (acetyl-CoA carboxylase), although there are many others.

As used herein, the term "AMPK activation" refers to the phosphorylation state of AMPK or a direct target thereof. AMPK may be activated by modulation of a protein upstream of AMPK (e.g., the adponectin receptor, the leptin receptor, the a-adrenergic receptor, or the insulin receptor etc.) or by AMPK itself. AMPK activation may be determined by assaying AMPK itself or a downstream target of AMPK.

An antibody that is specific for phospho-AMPK or a phosphorylated target thereof specifically binds the phosphorylated forms of those proteins but not the unphosphorylated forms of those proteins.

Other definitions of terms appear throughout the specification.

DETAILED DESCRIPTION

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Method of Sample Analysis

The method described below employs a sample of blood. However, blood is but one of many biological samples that can be employed in the method. In other embodiments, intact cells from other tissues (e.g., other soft tissues such as liver or spleen etc.) or cells grown in tissue culture may be employed. Methods for treating such tissues to provide a cell suspension suitable for flow cytometry are known. Once produced, a cell suspension may be employed in a similar way to that described below.

In general terms, the subject method involves: a) labeling cells of a blood sample using an antibody that specifically binds to phospho-AMPK or a phosphorylated target thereof, to produce a labeled sample; and b) measuring antibody binding by a population of blood cells of the labeled sample using flow cytometry, thereby obtaining an evaluation of AMPK activation in the population of blood cells. Since the results obtained from blood correlated well with results obtained from tissues associated with energy consumption (e.g., muscle or liver) the evaluation may of AMPK activation in blood can be extended to provided an evaluation of AMPK activation in the subject from which the blood was obtained.

While the method may be performed on whole blood, in particular embodiments, the population of blood cells analyzed may be white blood cells or a sub-population thereof (e.g., a lymphocyte population or a granulocyte population). In particular embodiments, the blood may contacted with a test agent ex vivo (i.e., using blood drawn from a subject) or in vivo (e.g., by administering the test agent to a mammal), and the results from the assay may be compared to results obtained from a reference sample of blood cells (e.g., blood cells that have not been in contact with the test agent or with a different amount of the test agent) to determine the effect of the compound on AMPK activation in the subject from which the blood sample was obtained.

Figure 2:
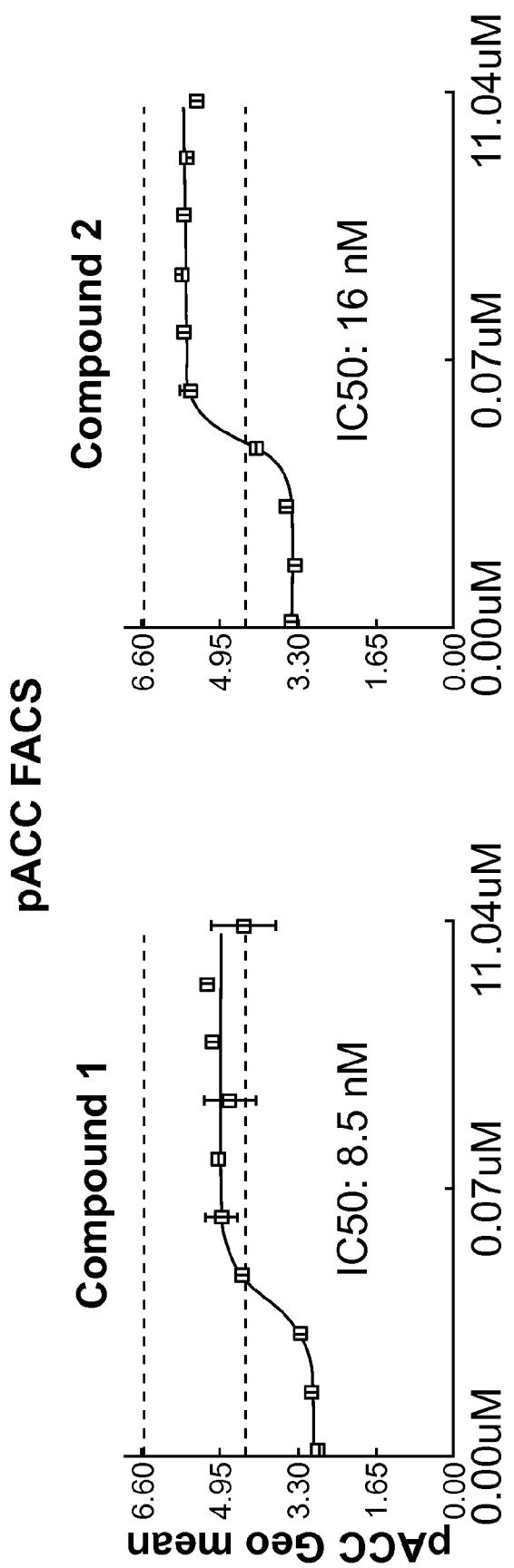
FIGS. 2A and 2B are graphs showing the results of a FACS-based AMPK activation performed on HepG2 cells.

The effect may in certain cases be measured by calculating the difference in geometric mean fluorescence of the population of blood cells and the geometric mean fluorescence of the reference sample of blood cells. As would be apparent, in certain embodiments, the contacting may involve administering the test agent to a subject and then drawing blood from the subject after a specified period of time. In other embodiments, the contacting may involve drawing blood from a subject and then contacting the agent with the drawn blood for a specified period of time. The test agent may or may not be a known modulator of the AMPK pathway. In particular embodiments, the reference sample may contain blood cells obtained from the same individual as the test blood sample. The reference sample may or may not have been contacted with the test agent. In particular cases, data obtained from the method may be expressed as a graph of the geometric means of fluorescence of number of samples, as illustrated in FIG. 2. Such a graph may show a time course, or the difference between different doses of a test agent, for example.

As illustrated in FIG. 1, AMPK acts as a metabolic master switch regulating several intracellular systems including the cellular uptake of glucose, the β-oxidation of fatty acids and the biogenesis of glucose transporter 4 (GLUT4) and mitochondria. The energy-sensing capability of AMPK can be attributed to its ability to detect and react to fluctuations in the AMP:ATP ratio that take place during rest and exercise (muscle stimulation). During muscle stimulation, AMP increases while ATP decreases, which changes AMPK into a good substrate for activation via an upstream kinase complex, AMPKK, or alternatively, where binding of AMP renders activated AMPK that is phosphorylated at Thr-172 a worse substrate for protein phosphatase 2Cα. AMPKK is a complex of three proteins, STE-related adaptor (STRAD), mouse protein 25 (MO25), and LKB1 (a serine/threonine kinase). During a bout of exercise, AMPK activity increases while the muscle cell experiences metabolic stress brought about by an extreme cellular demand for ATP. Upon activation, AMPK increases cellular energy levels by inhibiting anabolic energy consuming pathways (fatty acid synthesis, protein synthesis, etc.) and stimulating energy producing, catabolic pathways (fatty acid oxidation, glucose transport, etc.).

Triggering the activation of AMPK can be carried out provided that two conditions are met. First, the γ subunit of AMPK must undergo a conformational change so as to expose the active site (Thr-172) on the α subunit. The conformational change of the γ subunit of AMPK can be accomplished under increased concentrations of AMP. Increased concentrations of AMP will give rise to the conformational change on the γ subunit of AMPK as two AMP bind the two Bateman domains located on that subunit. It is this conformational change brought about by increased concentrations of AMP that exposes the active site (Thr-172) on the α subunit. This role of AMP is further substantiated in experiments that demonstrate AMPK activation via an AMP analogue 5-amino-4-imidazolecarboxamide ribotide (ZMP) which is derived from the familiar 5-amino-4-imidazolecarboxamide riboside (AICAR). The second condition that must be met is the phosphorylation and consequent activation of AMPK on its activating loop at Thr-172 of the α subunit brought about by an upstream kinase (AMPKK). The complex formed between LKB1 (STK 11), mouse protein 25 (MO25), and the pseudokinase STE-related adaptor protein (STRAD) has of late been identified as the major upstream kinase responsible for phosphorylation of AMPK on its activating loop at Thr-172. Although AMPK must be phosphorylated by the LKB1/MO25/STRAD complex, it can also be regulated by allosteric modulators which directly increase general AMPK activity and modify AMPK to make it a better substrate for AMPKK and a worse substrate for phosphatases. It has recently been found that 3-phosphoglycerate (glycolysis intermediate) acts to further pronounce AMPK activation via AMPKK.

CaMKK has also been identified as an upstream AMPKK. CaMKK phosphorylates and activates AMPK in an AMP-independent manner, which is triggered instead by a rise in the intracellular Ca2+ concentration. The discovery that CaMKK acts as an AMPKK indicates that in addition to an increase of the AMP-to-ATP ratio, AMPK may also be activated by a rise in the intracellular $Ca^{2+}$ concentration in response to nutrients, drugs, or physiological stimulation.

Some downstream targets of AMPK are illustrated in FIG. 1. As illustrated, downstream targets of AMPK include proteins that regulate carbohydrate metabolism (e.g., GEF, MEF, glycogen synthase, PFK2 and TORC2), lipid metabolism (e.g., HMGCoAR, ACC, HNF-4, SREBP-1 and HSL), cell growth and apoptosis (eNOS, p53, HrR and eEF2K) and protein metabolism. One exemplary downstream target of AMPK is acetyl-CoA carboxylase (ACC). Acetyl-CoA carboxylase is a biotin-dependent enzyme that catalyzes the irreversible carboxylation of acetyl-CoA to produce malonyl-CoA through its two catalytic activities, biotin carboxylase (BC) and carboxyltransferase (CT). ACC is a multi-subunit enzyme in the endoplasmic reticulum of most eukaryotes. The most important function of ACC is to provide the malonyl-CoA substrate for the biosynthesis of fatty acids. The activity of ACC can be controlled at the transcriptional level as well as by small molecule modulators and covalent modification. The human genome contains the genes for two different ACCs: ACACA and ACACB.

Phosphorylation of AMPK can result when the hormones glucagon or epinephrine bind to cell surface receptors, but the main cause of phosphorylation is due to a rise in AMP levels when the energy status of the cell is low, leading to the activation of the AMP-activated protein kinase (AMPK). AMPK is the main kinase regulator of ACC, able to phosphorylate a number of serine residues on both isoforms of ACC. On ACC1, AMPK phosphorylates Ser79, Ser1200, and Ser1215. On ACC2, AMPK phosphorylates Ser218. Protein kinase A also has the ability to phosphorylate ACC, with a much greater ability to phosphorylate ACC2 than ACC1. However, the physiological significance of protein kinase A in the regulation of ACC is currently unknown. When insulin binds to its receptors on the cellular membrane, it activates a phosphatase to dephosphorylate the enzyme; thereby removing the inhibitory effect.

AMPK and its targets are generally intracellular. As such, the method generally involves permeabilizing the blood cells, and then labeling the permeabilized cells using an antibody that specifically binds to phospho-AMPK or a phosphorylated target thereof. While the exact steps of such intracellular labeling methods may vary greatly, they generally involve permeabilizing the cells, labeling the cells using a labeled antibody and then fixing the stained cells so that the contents of the cells stay intact during subsequent manipulations. Exemplary methods by which cells can be labeled using fluorescent antibodies that are specific for intracellular proteins are described in a variety of publications, including: Lazarus et al (Cytometry. 1998 32:206-13), Sartor et al (Cytometry. 1994 18:119-22), Gadol et al (Cytometry 1994 15:359-70) and Far et al (Cytometry. 1994 15:327-34), which are incorporated by reference for disclosure of these methods. Kits for intracellularly labeling cells for FACS analysis include the INTRACYTE™ intracellular FACS kit by Orion BioSolutions, Inc (Vista Calif.), the INTRASURE™ or FASTIMMUNE™ kits by Becton Dickinson (Franklin Lakes, N.J.) and the CYTOFIX™ or CYTOPERM™ Plus kits by PharMingen (San Diego, Calif.). Depending on the method employed, the red blood cell of the sample may be lysed prior to permeablizing and labeling of the white blood cells. Such lysis techniques may be adapted from those commonly employed in blood analysis.

Antibody binding by individual cells of the population of blood cells is measured using flow cytometry. Such methods are known and reviewed in a variety of publications, including Brown et al (Clin Chem. 2000 46:1221-9), McCoy et al (Hematol. Oncol. Clin. North Am. 2002 16:229-43) and Scheffold J. Clin. Immunol. 2000 20:400-7) and books such as Carey et al (*Flow Cytometry in Clinical Diagnosis*, 4$^{th}$ Edition ASCP Press, 2007), Ormerod (*Flow Cytometry—A practical approach* 3rd Edition. Oxford University Press, Oxford, UK 2000), Ormerod (*Flow Cytometry* 2nd Edition. BIOS Scientific Publishers, Oxford, UK 1999) and Ormerod (*Flow Cytometry—A basic introduction* 2009 Cytometry Part A 75A, 2009), which are all incorporated by reference herein for disclosure of those methods.

Figure 3:
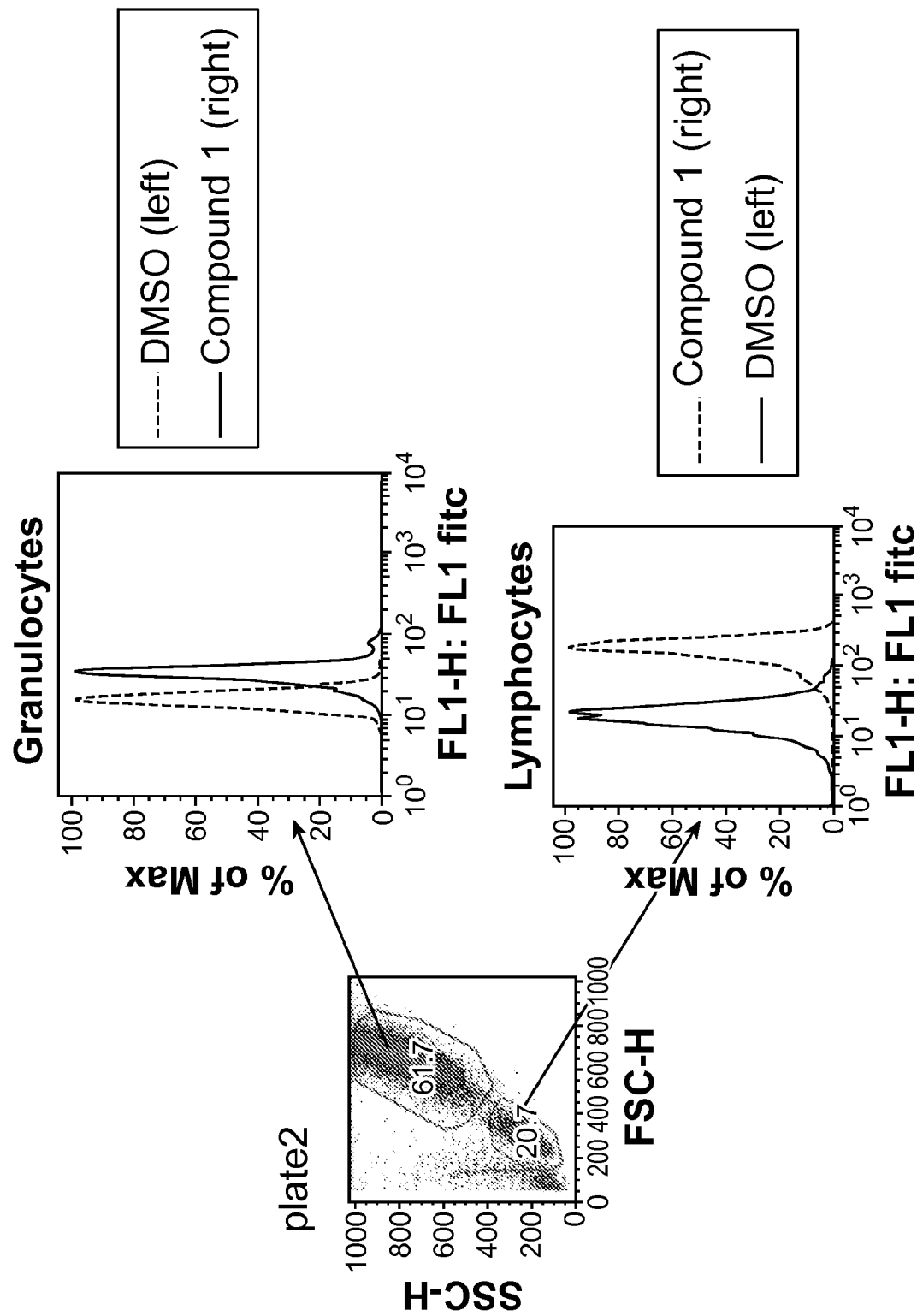
FIG. 3 shows the results of a pAMPK FACS assay using human whole blood. The results show a 7-fold window for lymphocytes.

In particular cases, the data for a single sample may be processed to provide the number of events for each a measurement of fluorescence. As shown in FIG. 3, the data may in certain cases be expressed as a single parameter histogram that shows the units of fluorescence on the x axis and the cell count on the y axis. The fluorescence may be a log value and in certain cases may be the log of an absolute (e.g., raw) or normalized value. The peak of the histogram provides an evaluation of AMPK activation in the subject from which the blood sample was obtained. The peak of the histogram can be the geometric mean of the fluorescence values, however other statistical analysis can be employed to provide a similar result. Since the various sub-populations of blood cells (i.e., red blood cells, platelets and white blood cells which are composed of neutrophils, lymphocytes, monocytes, eosinophils, and basophils) are readily distinguishable using flow cytometry, the data may be analyzed to provide an evaluation of AMPK activation in any sub-population of blood cells. In one embodiment, the data may be analyzed to provide an evaluation of AMPK activation in lymphocytes. In a further embodiments, the blood cells may be labeled with a second antibody, e.g., a cell surface antibody, and the data may be analyzed to provide an evaluation of AMPK activation in cells that are labeled with the second antibody.

The methodology described herein may be generally employed on any suitable flow cytometer, examples of which are known on the art and described in, e.g., U.S. Pat. Nos. 5,378,633, 5,631,165, 6,524,858, 5,266,269, 5,017,497 and 6,549,876, PCT publication WO99/54494 and as well as published U.S. Patent Applications US20080153170, 20010006787, US20080158561, US20100151472, US20100099074, US20100009364, US20090269800, US20080241820, US20080182262, US20070196870 and US20080268494, each of which are incorporated by reference herein).

The antibody used to label the cells should be capable of specifically binding to native (i.e., folded) phospho-AMPK or a phosphorylated target thereof. In particular cases, antibody may binds at much reduced (i.e., by a factor of at least 2, 5, 10, 50 or 100) affinity to the linear (i.e., unfolded, denatured) form of the protein. The structure to which such an antibody binds contains may amino acid that are dis-contiguous in the protein. In other words, in certain cases binding of such an antibody to a polypeptide may be dependent upon the polypeptide being folded into a particular three dimensional conformation.

Such antibodies may be made by, e.g., immunizing a suitable animal, e.g., a warm-blooded animal, in particular a mammal such as a rabbit, mouse, rat, camel, sheep, cow or pig or a bird such as a chicken or turkey, with a folded phospho-AMPK or downstream target thereof using any of the techniques well known in the art suitable for generating an immune response. Procedures for immunizing animals are well known in the art, and are described in Harlow (*Antibodies: A Laboratory Manual*, First Edition (1988) Cold Spring Harbor, N.Y.) and Weir (*Handbook of Experimental Immunology* Vol 4, Blackwell Scientific Publishers, Oxford, England, 1986). As will be appreciated by one of ordinary skill in the art, the immunogen may be admixed with an adjuvant or hapten in order to increase the immune response (for example, complete or incomplete Freund's or lipid A adjuvant), or with a carrier such as keyhole limpet hemocyanin (KLH).

Once a suitable animal has been immunized and an immune response against the antigen has been established by the animal, antibody producing cells from the animal are screened to identify cells that produce antibodies having a desired activity. In some embodiments, these methods may employ hybridoma technology in which cells from the spleen of the immunized animal are fused with a suitable immortal cell to produce hybridoma cells. Supernatants from these hybridoma cells may be screened, and positive clones are expanded according to standard procedures (Harlow et al. *Antibodies: A Laboratory Manual*, First Edition (1988) Cold spring Harbor, N.Y.; and Spieker-Polet et al., supra).

The antibodies may be screened for binding to phosphorylated AMPK or phosphorylated target thereof folded into a native conformation by, e.g., cell staining to identify those antibodies that are specific for phosphorylated forms of these proteins. In particular embodiments, commercially available antibodies may be screened to identify a suitable antibodies.

In alternative embodiments, a phage display antibody may be employed, methods for the production of which are well known (see, e.g., Scott et al. Science 1990 249: 386; Devlin et al., Science 1990 249: 404; U.S. Pat. Nos. 5,223,409, 5,733,731, 5,498,530, 5,432,018, 5,338,665, and 5,922,545, for example).

In particular cases, rather than an antibody that is specific for AMPK or a downstream target thereof, the method described above and below may be performed using an antibody that is specific for a phosphorylated AMPK-related kinase (e.g., BRSK1, BRSK2, NUAK1, NUAK2, QIK, QSK, SIK, MARK1, MARK2, MARK3, MARK4, MELK, or SNARK; Manning et al, Science 2002 298: 1912-1934) which are closely related to AMPKα1 and AMPKα2, some of which have also been implicated in energy homeostasis (Koh et al PNAS 2010 107: 15541-15546).

In alternative embodiments, a quantitative western blotting method, e.g., using a capillary-based system such as a Cell Biosences CB1000 machine, may be employed. Alternatively, mass spectrometry or mass cytometry may be employed. In certain cases, the assays may be done on a high throughput format, e.g., using 96- or 384-well plates.

Utility

The method described above may be employed to identify compounds that modulate AMPK activation, to determine whether an administered compound is having a desired effect, or to determine an optimal dose of a compound is known to modulate AMPK activation, for example. In these embodiments, the measurement obtained using the above method may be compared to results obtained from a reference sample of blood. As noted above, the test sample of blood may be contacted with a test agent ex vivo or in vivo. The reference sample of blood may not have been contacted with the test agent or may have been contacted with a different amount of the test agent, for example. In one embodiment, both the test and reference samples may have been contacted with the same amount of the test compound, but at different times or for different durations. The test and reference samples may be obtained from the same subject, or from different subjects. The subject may have fasted for at least 8-12 hours, or, in certain cases, the method may be performed before, during or after exercise. The method may be coupled with other medical tests, such as a cholesterol test (i.e., a lipid panel) or a blood glucose test to provide an evaluation of the health of the subject. The target of the test agent may be upstream of AMPK, may be AMPK itself, or downstream of AMPK. In some cases, the mechanism of action a test agent may be unknown.

In one exemplary embodiment, separate aliquots of blood from the same individual are contacted with two or more amounts of a test agent that is known to modulate AMPK activation. The contacted blood may be assayed using the method described above, and an effective dose of the test agent may be determined.

In another exemplary embodiment, separate aliquots of blood from the same individual are contacted with: a) a test agent that is not known to modulate AMPK activation and b) a control solution that does not contain the test agent. The contacted blood may be assayed using the method described above, and the effect of the compound on AMPK activation is be determined.

In these embodiments, the degree to which the test sample and control sample differ may be determined by comparing, for example, the geometric mean of the results obtained from a test sample to the geometric mean of the results obtained from a reference sample. A greater difference between the geometric means indicates that the agent has a greater effect on AMPK activation. For example, as illustrated in FIG. 3, the Compound 1 has a greater effect on AMPK activation in lymphocytes than in granulocytes. Relative to the geometric mean fluorescence of a sample that had not been contacted with the compound, a compound that modulates AMPK activation may alter the geometric mean fluorescence by at least 5%, at least 10%, at least 20%, or at least 50%. In particular embodiments, the compound may lead to a decrease of at least 10%, at least 20%, at least 50%, at least 70% or at least 80% in the geometric mean fluorescence. In other embodiments, the compoud may lead to an increase of at least 10%, at least 20%, at least 50%, at least 70%, at least 100% or at least 200% or at least 500% or more in the geometric mean fluorescence.

As noted above, the test agent may be administered in vivo, in which case, the contacting may comprise administering the test agent to a subject and then drawing blood from the subject after a specified period of time (e.g., from 5 minutes to 1 hr, 1 hr to 12 hr, 12 hr to 24 hr or 24 hr to 1 week or more) prior to analysis by flow cytometry. In ex vivo applications, the contacting may comprise drawing blood from a subject and then contacting the test agent with the drawn blood for a specified period of time (e.g., from 5 minutes to 1 hr, 1 hr to 12 hr, 12 hr to 24 hr or 24 hr to 1 week or more) prior to analysis by flow cytometry.

In one in vivo embodiment, one amount of an AMPK modulator may be administered to a subject and, after a specified period of time, blood may be drawn from the subject and assayed using the method described above. Based on the results of the assay, a second amount of the AMPK modulator may be administered to the subject and, after a specified period of time, blood may be drawn from the subject and assayed using the method described above. These steps may be repeated until a desired effect (e.g., a dose of the AMPK modulator that results in a desired, stable, level of AMPK activation) is achieved. This method may be used to optimize the dosage of an AMPK modulator for a particular subject.

In general terms the blood used in the assay may be obtained from any mammalian subject including the orders carnivore (e.g., dogs and cats), rodentia (e.g., mice, guinea pigs, and rats), and primates (e.g., humans, chimpanzees, and monkeys). In some embodiments, the subject may be human. The subject may be healthy or in some cases may have cancer, an inflammatory disease or a metabolic disease such as obesity or diabetes. In particular embodiments, the subject may have one or more risk factors for metabolic syndrome, such as, stress, overweightness, sedentary lifestyle, aging, coronary heart disease, chronic heart failure, lipodystrophy, schizophrenia, peripheral artery disease, neurodegenerative diseases, muscle atrophy/weakness/myopathy, renal diseases, chronic obstructive pulmonary disease, age-related macular degeneration, or rheumatic disease. For example, a subject may have fasting hyperglycemia (caused by, e.g., diabetes mellitus type 2 or insulin resistance), high blood pressure, central obesity, decreased HDL cholesterol and/or elevated triglycerides.

In some embodiments, the test agent may be known to affect AMPK activation. Such agents are known and include: metformin, cilostazol, 5-aminoimidazole-4-carboxamide ribonucleoside (AICAR), 2-deoxyglucose, thiazolidinediones such as troglitzone rosiglitazone, resveratrol, and pioglitazone, as well as a variety of other compounds described in PCT publications WO08/083,124, WO09/065,131, WO09/076,631, WO09/132,136, and WO10/088,392. published U.S. patent applications US20100009992, US20090253764, US20090105293, US20090094709, US20080221088, US20070244202, US20070054965, US20070015665, US20060287356, US20060134240, US20050038068 and U.S. Pat. No. 7,119,205, the disclosures of which are incorporated by reference for generic and specific disclosure of those compounds.

In other embodiments, the effect of the test agent on AMPK activation may be unknown. Such agents may be from any chemical class and in certain cases may be synthetic, semi-synthetic, or naturally-occurring inorganic or organic molecules. Test agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). Alternatively, libraries of natural compounds in the form of bacterial, fungal, plant and animal extracts are available from Pan Labs (Bothell, Wash.) or are readily producible.

Test agents may be small organic or inorganic compounds having a molecular weight of more than 50 and less than about 2,500 Da. Test agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Test agents may be obtained from a wide variety of sources including libraries of synthetic or natural compounds. For example, numerous means are available for random and directed synthesis of a wide variety of organic compounds and biomolecules, including expression of randomized oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Screening may be directed to known pharmacologically active compounds and chemical analogs thereof, or to new agents with unknown properties such as those created through rational drug design.

The subject may contacted with the candidate agent, e.g., the agent is administered to the animal by any acceptable route of administration, including, but not limited to, oral (e.g., oral gavage), intravenous, intramuscular, intranasal, subcutaneous, intragastric, etc., e.g., any enteral or parenteral route. A single dose is administered, or multiple doses over a period of time are administered.

Formulations, including pharmaceutical formulations, comprising an agent identified by a screening method presented herein, are provided. A formulation comprises an effective amount of an agent. An "effective amount" means a dosage sufficient to produce a desired result.

Although the dosage used will vary depending on the clinical goals to be achieved, a suitable dosage range is one which provides up to about 1 µg to about 1,000 µg or about 10,000 µg of an agent that produces a desired result can be administered in a single dose. Alternatively, a target dosage of an agent that produces a desired result can be considered to be about in the range of about 0.1-1000 µM, about 0.5-500 µM, about 1-100 µM, or about 5-50 µM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

In particular embodiments, the subject method may be employed to provide a read-out of the metabolic health of a subject in a similar way as a glucose or cholesterol test. The subject method may be performed alone, or in combination with other clinical techniques (e.g., a physical examination or another blood test). For example, results obtained from the subject assay may be combined with other information, e.g., information regarding blood glucose levels, weight, or other proteinaceous blood markers that indicate the metabolic health of an individual.

In one exemplary embodiment, prior to the labeling of the cells, the method may comprise subjecting a mammal to a change in lifestyle (e.g., a change in diet or amount of exercise), and obtaining a blood sample from the mammal that is subsequently analyzed. The evaluation may then be compared to results obtained from a reference sample of blood cells, thereby determining the effect of the change in lifestyle on AMPK activation of the mammal.

In one embodiment, a sample may be collected from a patient at a first location, e.g., in a clinical setting such as in a hospital or at a doctor's office, and the sample may be forwarded to a second location, e.g., a laboratory where it is processed and the above-described method is performed to generate a report. A "report" as described herein, is an electronic or tangible document which includes report elements that provide test results that may include the geometric mean obtained from the test as well as, for example, a range of geometric means that are considered "normal". Once generated, the report may be forwarded to another location (which may be the same location as the first location), where it may be interpreted by a health professional (e.g., a clinician, a laboratory technician, or a physician such as an oncologist, surgeon, pathologist), as part of a clinical diagnosis.

EXAMPLES

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Three different AMPK activators employed in the examples described below. Compound 1 is described in PCT publication WO10/088,392, Compound 2 is described in PCT publication WO09/065,131.

Example 1

MEF or C2C12 cells were treated with DMSO or Compound 2 and probed by western blotting with a Cell Signaling anti-pAMPK antibody. The antibody exclusively recognized pAMPK and no other bands are observed. The same antibody was used for FACS in subsequent experiments.

HepG2 human liver cancer cells were trypsinized, resuspended in a complete media at $2 \times 10^6$ cells per ml and plated in a deep well round-bottom 96-well plate, 100 µl per well. Compound was added in 1 µl of DMSO to the cell suspension, mixed and incubated 1 hr at 37° C. Following the incubation, 900 µl of lyse-fix solution (BD) was added and the plate was incubated at 37° C. for another 10 min, spun for 5 min and the supernatant removed. Cell pellet was resuspended in 250 µl of ice-cold methanol and incubated for 30 min at 4° C. Following a transfer to a regular 96-well round-bottom plate, the cells were spun down for 5 minutes, washed in 250 µl of PBS containing 2% of FCS (PBS2) and resuspended in 100 µl of PBS2 containing 1:100 dilution of pACC antibody (Millipore). Suspension was incubated overnight at room temperature on a shaker. The following morning, cells were washed once with PBS2 and incubated with secondary goat anti-rabbit antibody conjugated to Alexa 488 at 1:200 dilution for 1 hr at room temperature. After a singl wash, the cells were sorted on a BD FACS sorter. Quantitation was performed using Flowjo software. Geometric mean of a Alexa 488 signal for live cells gate was used to plot the results and determine $EC_{50}$ in matlab.

Results are shown in FIG. 2. $EC_{50}$s obtained by FACS strongly correlate with the in-cell western ones for the same epitope, validating the FACS-based approach.

Example 2

Whole human blood was aliquoted at 100 µl per well into round-bottom plate, 1 µl of 1 uM Compound 1/DMSO solution or DMSO alone was added, mixed and incubated for 1 hr at 37° C., then 900 µl of lyse-fix solution (BD) was added. The rest of the procedure was performed as described for HepG2 cells above, except pAMPK rabbit antibody (Cell Signaling) at 1:100 dilution was used instead of pACC as a primary. Lymphocytes and granulocytes were gated as indicated.

Results are shown in FIG. 3. The 4-7 fold greater signal window allows to create a robust blood-based assay.

Example 3

Whole human and mouse blood was aliquoted at 100 µl per well into round-bottom plate, 1 µl of 1 uM Compound 1

Figure 4:
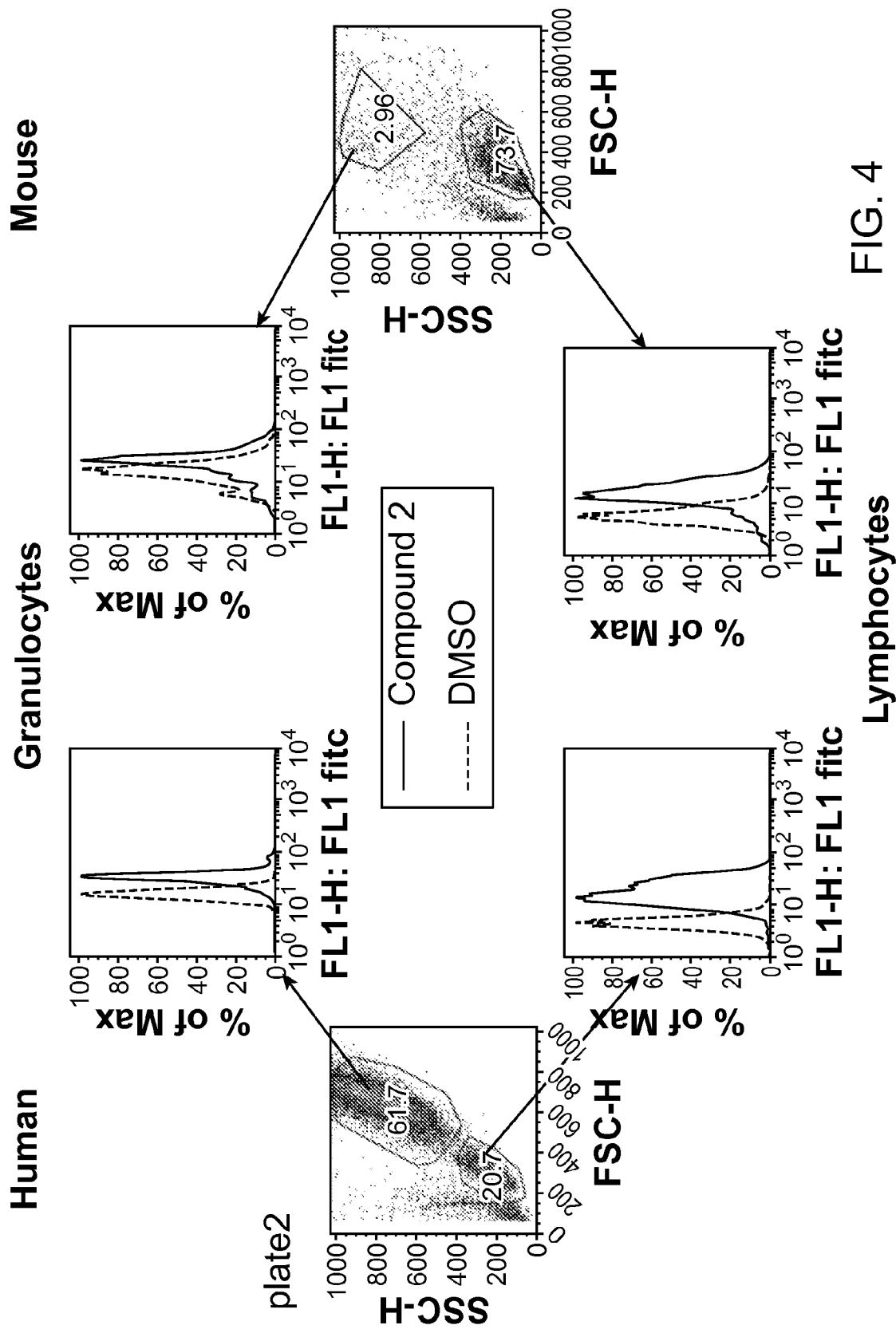
FIG. 4 shows the results of a pAMPK FACS assay in human and mouse whole blood. The protocol was the same as that used for the data shown in FIG. 3. The results show a robust window in lymphocytes. The control peak is on the left of each of each graph, and the peak for compound 2 is on the right.

DMSO solution or DMSO alone was added, mixed and incubated for 1 hr at 37° C., then 900 µl of lyse-fix solution (BD) was added. The rest of the procedure was performed as described for HepG2 cells above, except pAMPK rabbit antibody (Cell Signaling) at 1:100 dilution was used instead of pACC as a primary. Results are shown in FIG. 4. The antibody works both using human and rodent blood.

Example 4

FL-1 channel histograms for gated human or mouse lymphocytes and granulocytes stained for pAMPK were compared. In both species lymphocytes consistently demonstrated better window than granulocytes. Purified T-cells propagated in the presence of IL-2 proved to be poor replacement for the whole blood due to a very narrow window of stimulation. As a result, all the follow up experiments used WB lymphocytes to generate EC50.

Example 5

Figure 5:
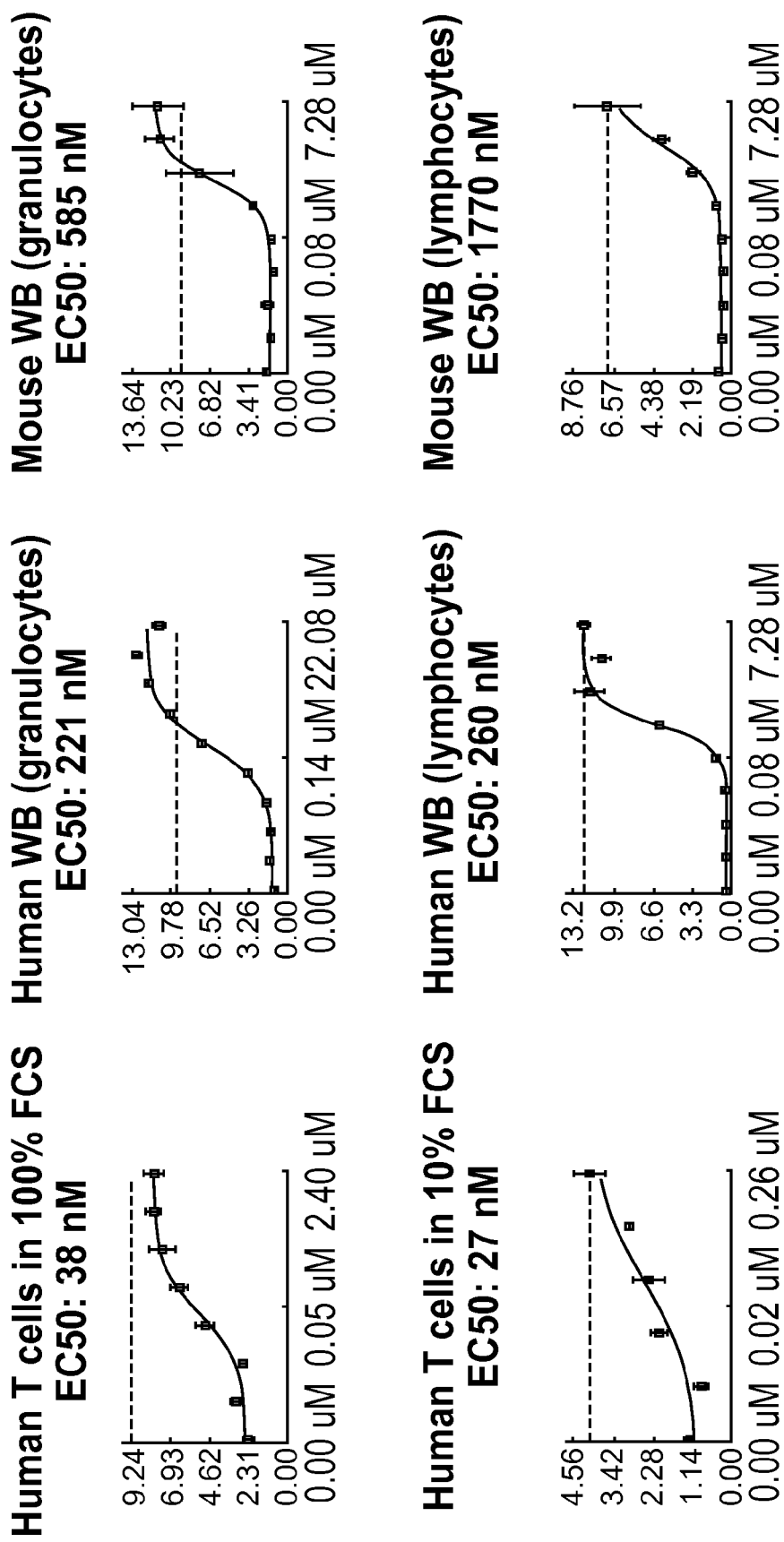
FIG. 5 shows results of a pAMPK FACS assay using mouse whole blood. Compound 2, a known modulator of AMPK, is used as the test compound.

EC50 determination for stimulation of AMPK phosphorylation by Compound 2 in propagated in vitro human T-cells and in human and mouse blood cells. Results are shown in FIG. 5. Window for purified T-cells is very narrow due to high background level of AMPK phosphorylation, presumably induced by cell stress. EC50 for mouse blood is significantly (about 10 fold on average) higher than that of a human. Both human and mouse EC50s are significantly higher than the corresponding EC50 for HepG2 (up to few hundred fold)

Example 6

Effects of starvation on AMPK phosphorylation in mouse blood. C57B1/6J male mice were either fasted for 14 hrs or fed normally prior to blood collection. AMPK stimulation by the Compound 2 and Compound 1 was performed ex vivo for 1 hr in 50 µl. Staining procedure was same as for the HepG2, except 1:500 dilution for both primary and secondary antibodies was used. Maximum level of AMPK phosphorylation in fasted animals was consistently higher by almost 2 fold when compared to the fed ones, while the background level remained intact.

Example 7

Figure 6:
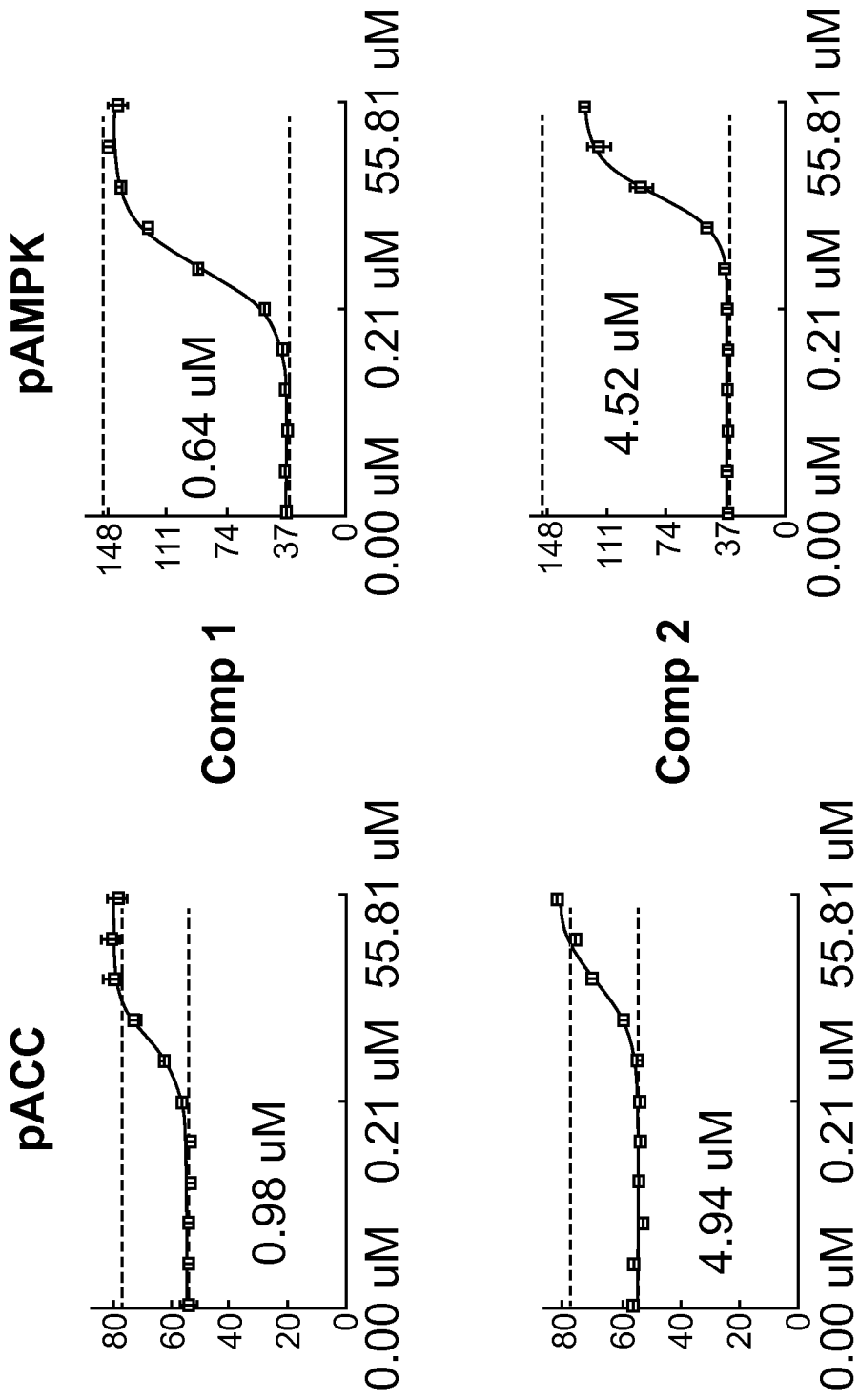
FIG. 6 shows results of a FACS assay showing that $EC_{50}$ data obtained for pACC correlates with $EC_{50}$ data for pAMPK.

Effects of starvation on ACC phosphorylation by AMPK in mouse blood. All the observations for AMPK phosphorylation are relevant to pACC staining as well. Results are shown in FIG. 6. EC50s for both proteins are identical when same compound is used, as expected.

Example 8

Staining using anti-pAMPK rabbit monoclonal and polyclonal antibody is highly specific and donor-independent. Whole blood samples from two human donors were used to stain for pAMPK in the absence (blue profile) and in the presence (red profile) of 10 µM of Compound 2 that induces AMPK phosphorylation. Both antibodies robustly detected similar increase in AMPK phosphorylation upon Compound 2 treatment, confirming selectivity of staining.

Example 9

Figure 7:
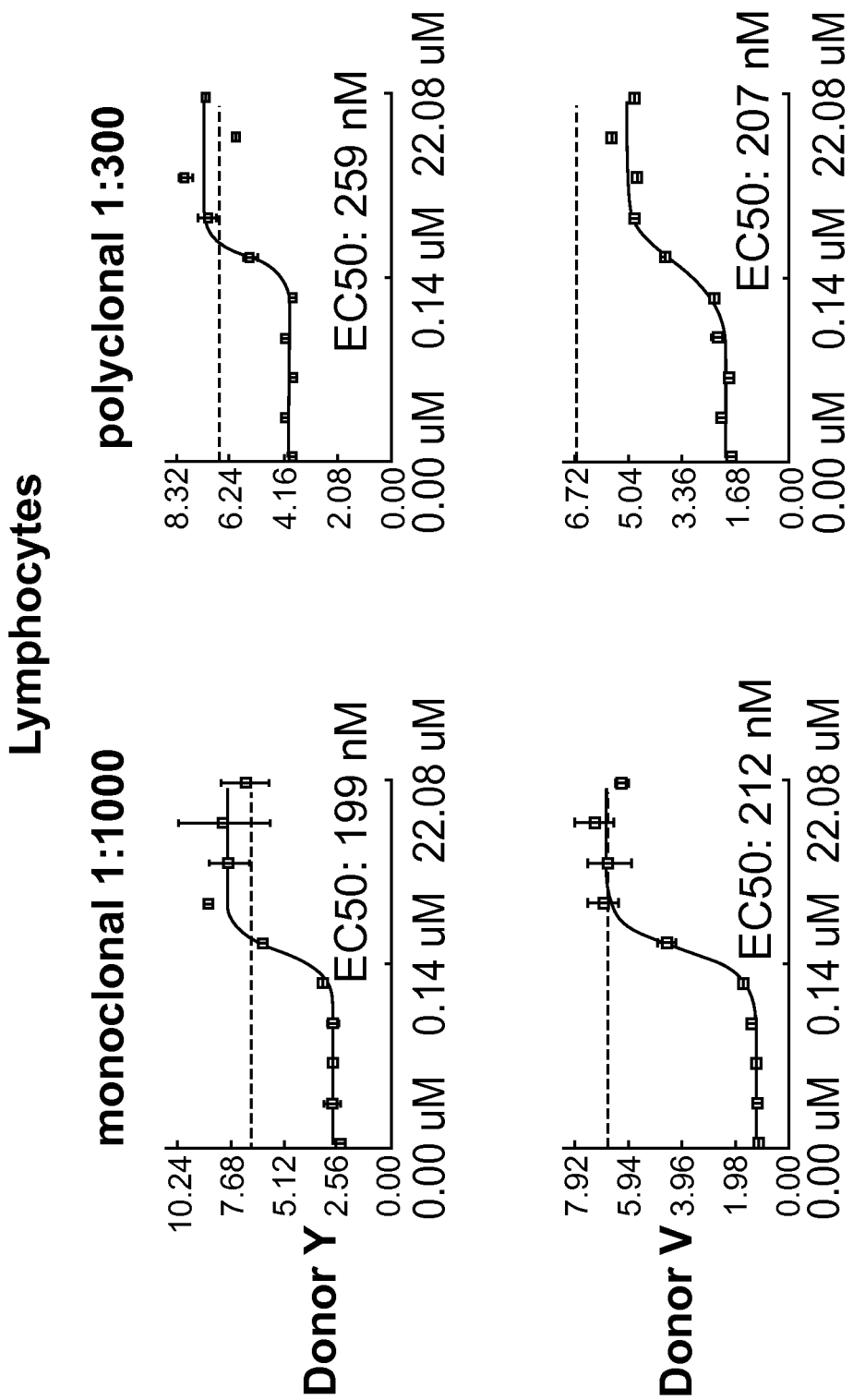
FIG. 7 is a series of graphs showing that the pAMPK human whole blood FACS assay is highly specific in that different donors and different antibodies provide very similar results.

EC50 for Compound 2 in human whole blood from two different donors were identical when using two different antibodies for staining of lymphocytes. Results are shown in FIG. 7. Window was significantly better when using monoclonal rabbit antibody.

Example 10

The curves obtained by staining the blood cells for pAMPK after titrating compound in whole blood ex vivo are more reproducible when using lymphocyte gate rather than the granulocyte one, but EC50 obtained by both methods are essentially the same irrespectable of the antibody, cell type or donor.

Example 11

Figure 8B:
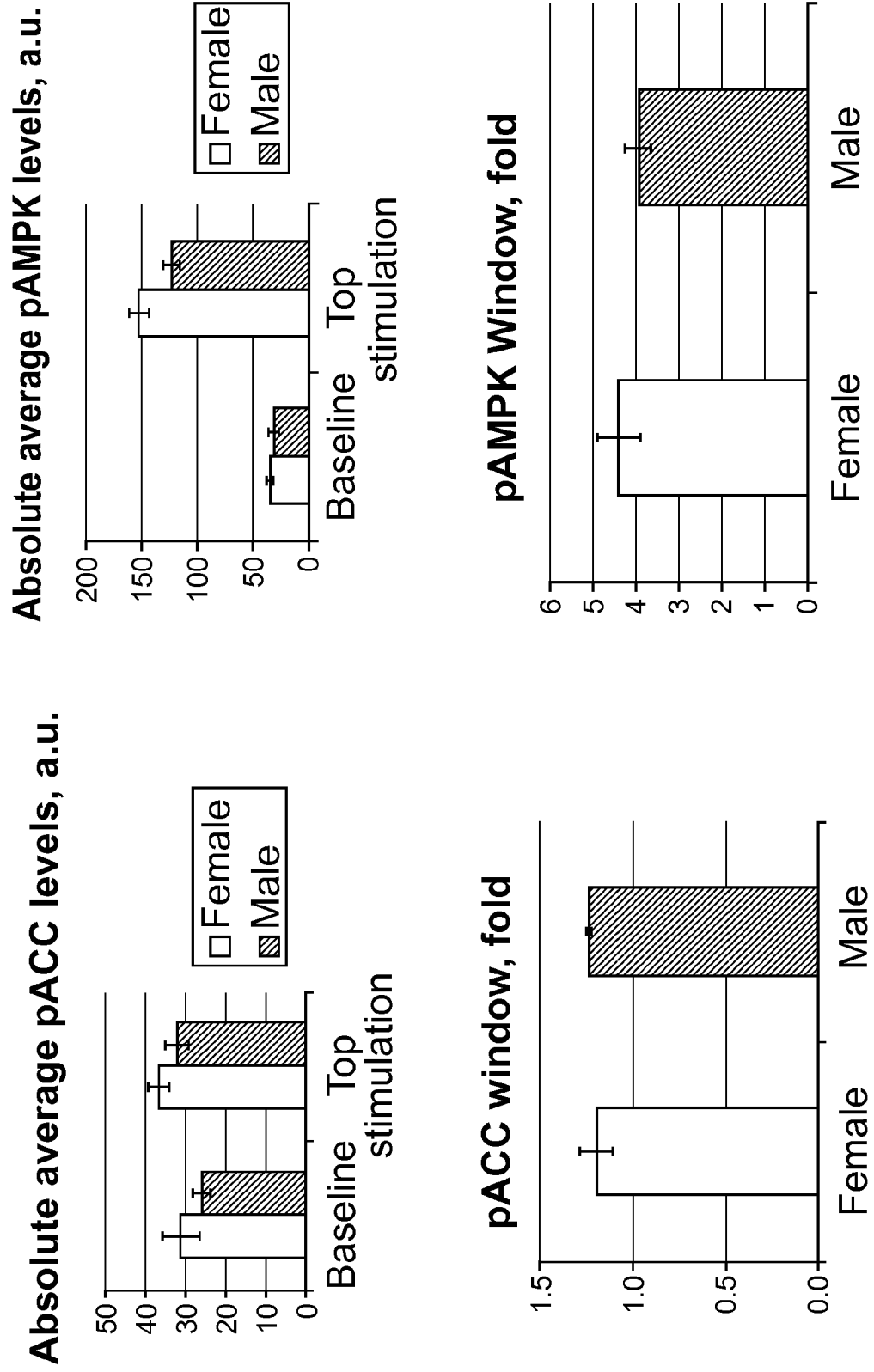

Consistency and stability of the pAMPK assay. Titration curves and EC50s for Compound 1 and Compound 2 obtained at different weeks using the blood of the same donor. The final EC50s are closely matching each other. FIG. 8A-8C shows that there is low donor to donor variability in pAMPK and pACC stimulation using two AMPK activators.

Example 12

Figure 9:
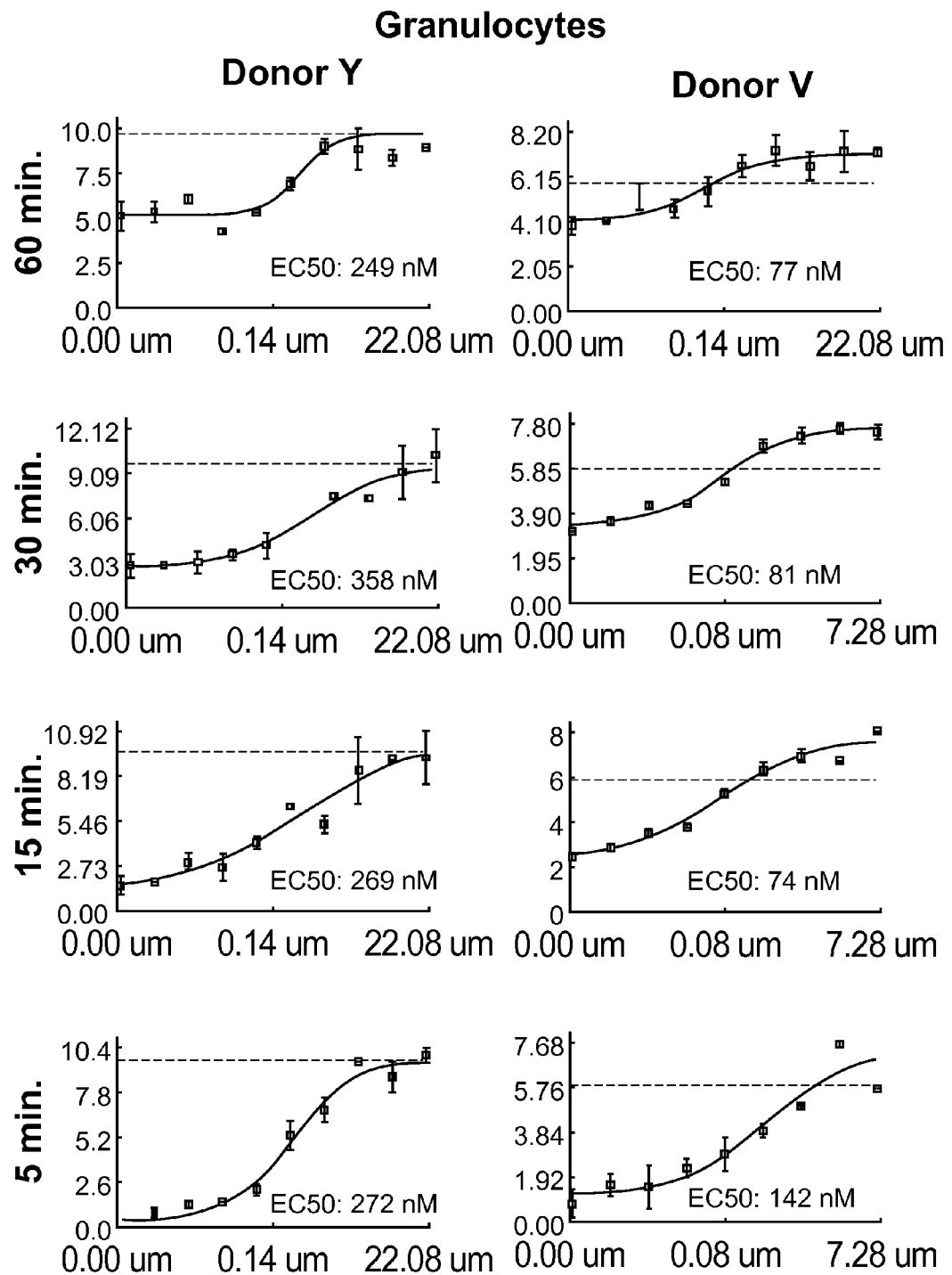
FIG. 9 is a series of graphs showing the effect of incubation time on the EC50 of Compound 2, a known modulator of AMPK.
Figure 9:
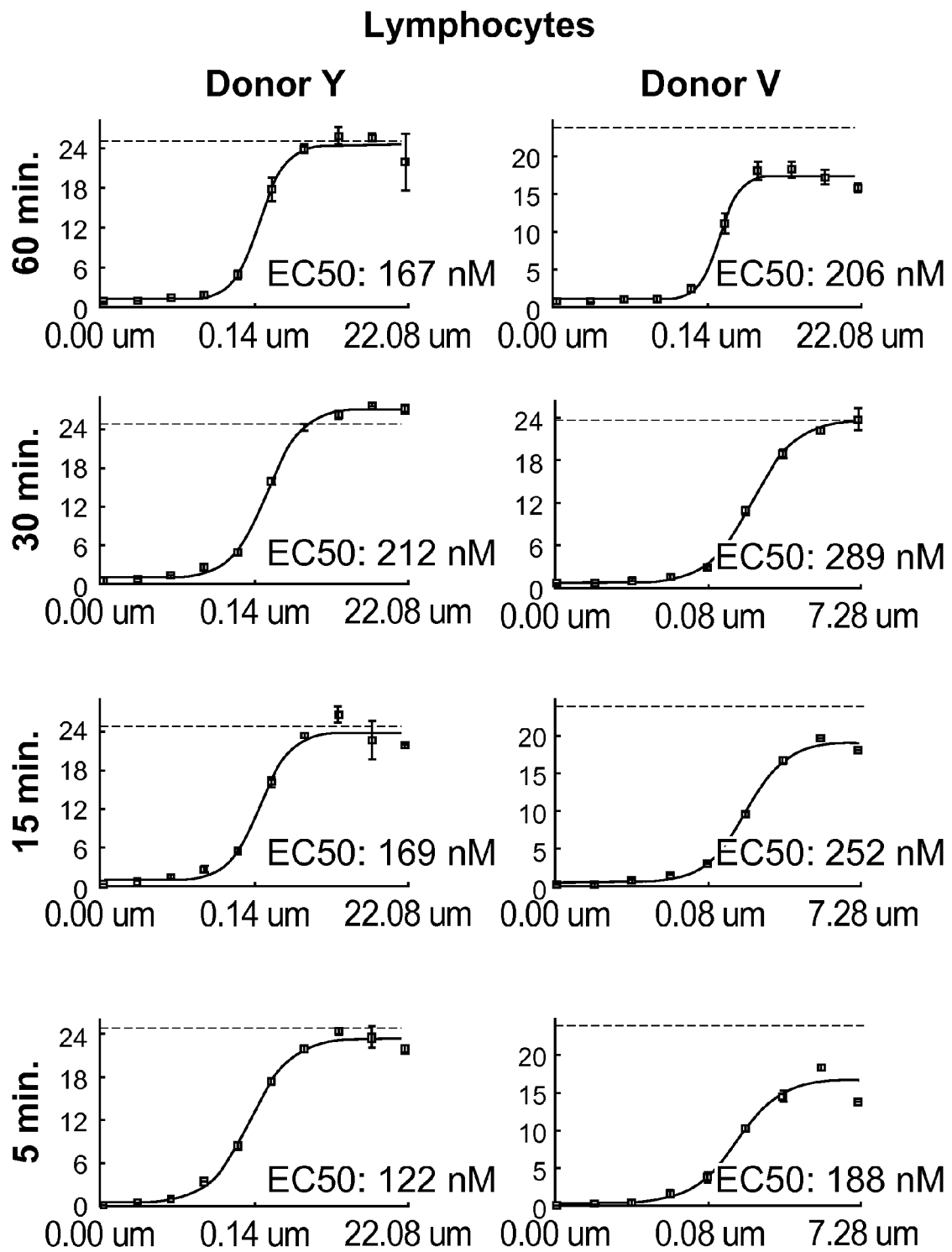

Effects of incubation time with the compound on resulting EC50 in a WB assay. Human whole blood from the single donor was treated with various amounts of compound 1 for given time periods at 37° C. The blood was processed according to the standard method to detect AMPK phosphorylation by FACS. $EC_{50}$ s were determined by matlab. Results are shown in FIG. 9. Very little effect on lymphocytes was observed (right 2 panels). Granulocytes are extremely sensitive to the incubation time due to a significant and steady upward drift in a baseline level of pAMPK detected, even though it does not result in significant change in EC50 (left 2 panels). Thus, longer incubation time unexpectedly decrease the window and general robustness of the assay. In both cell types, Compound 2 demonstrates an extremely fast kinetics of AMPK activation—at 5 min interval one can see a complete stimulation of the kinase at saturating concentrations of the compound. Maximal activation level remains the same, unstimulated levels increase marginally.

Example 13

Figure 10:
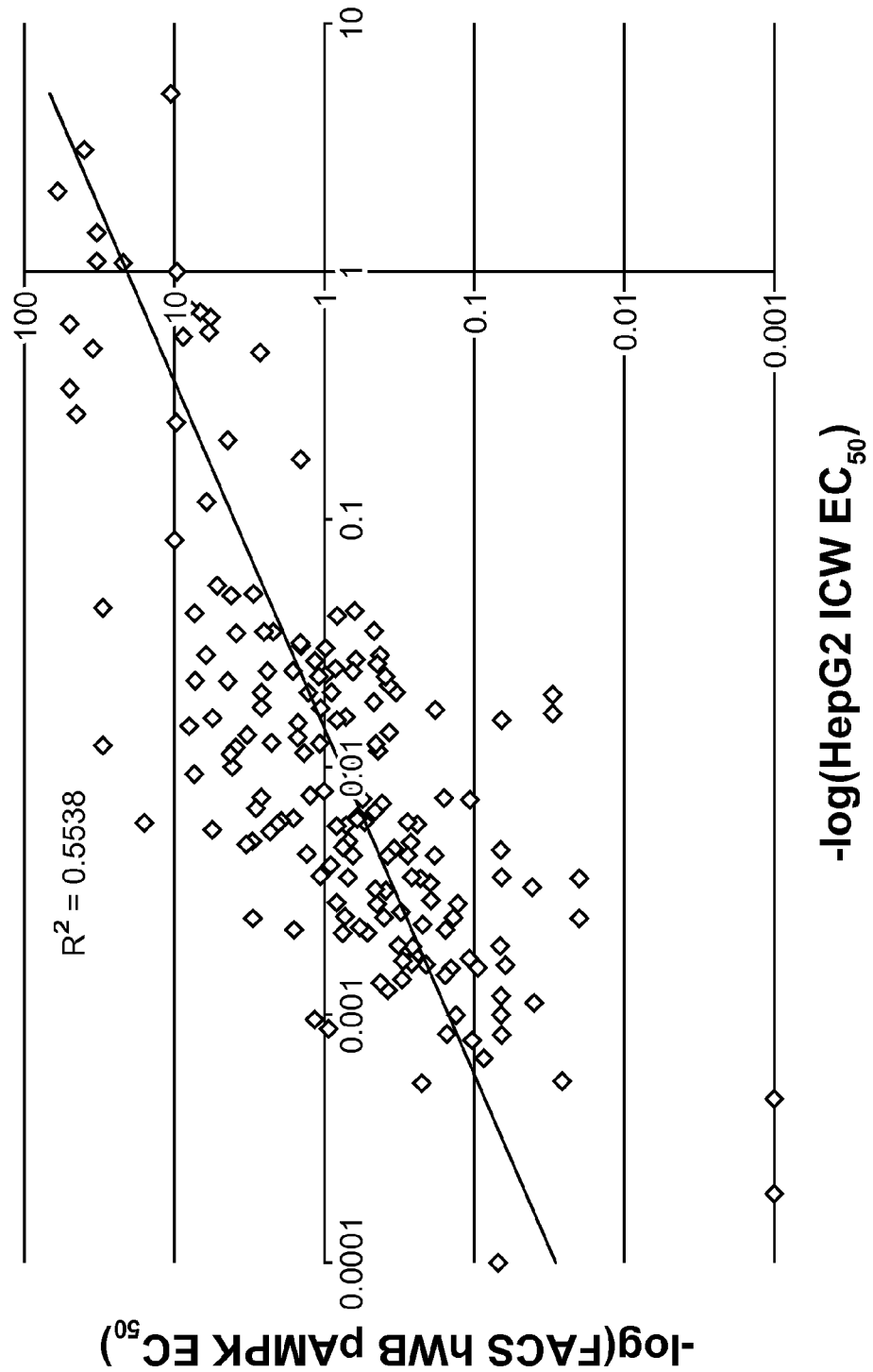
FIG. 10 is a scatter plot that shows the correlation between pAMPK assays using human white blood cells and HepG2 cells. 200 compounds were tested.

FIG. 10 shows a strong linear correlation between EC50s obtained by pACC in-cell-western (ICW) in HepG2 cells (X axis) and those obtained by pAMPK FACS in human whole blood (Y axis). Logarithmic scale for both axis' was used. Majority of the compounds demonstrate a significant loss of potency (up to 100 fold) in the blood compared to HepG2 cells, presumably due to combination of high protein binding and high level of distribution into red blood cells (high VSS) for the compounds tested.

Example 14

Figure 11:
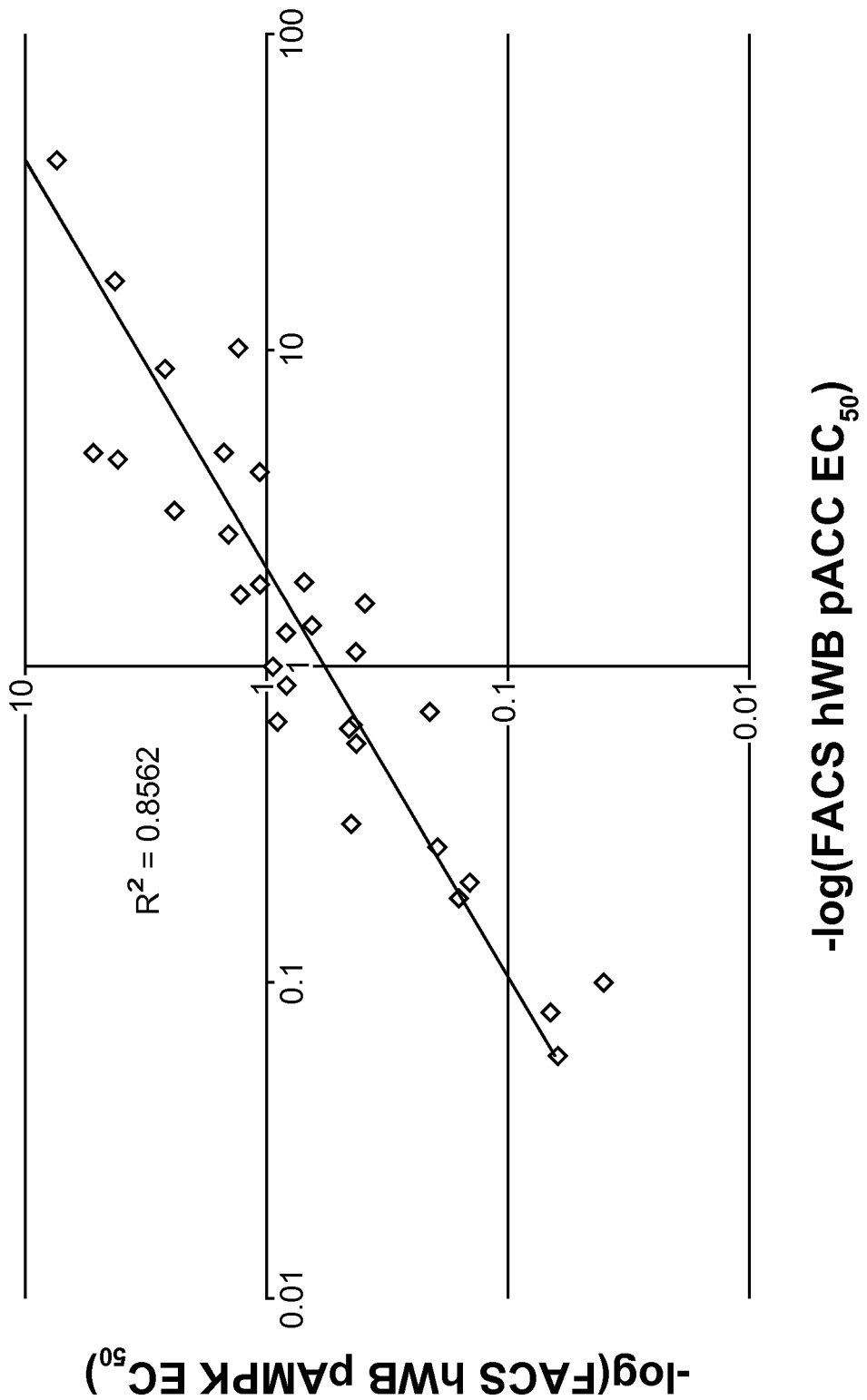
FIG. 11 is a scatter plot showing the correlation between pAMPK and pACC using human white blood cells.
Figure 12:
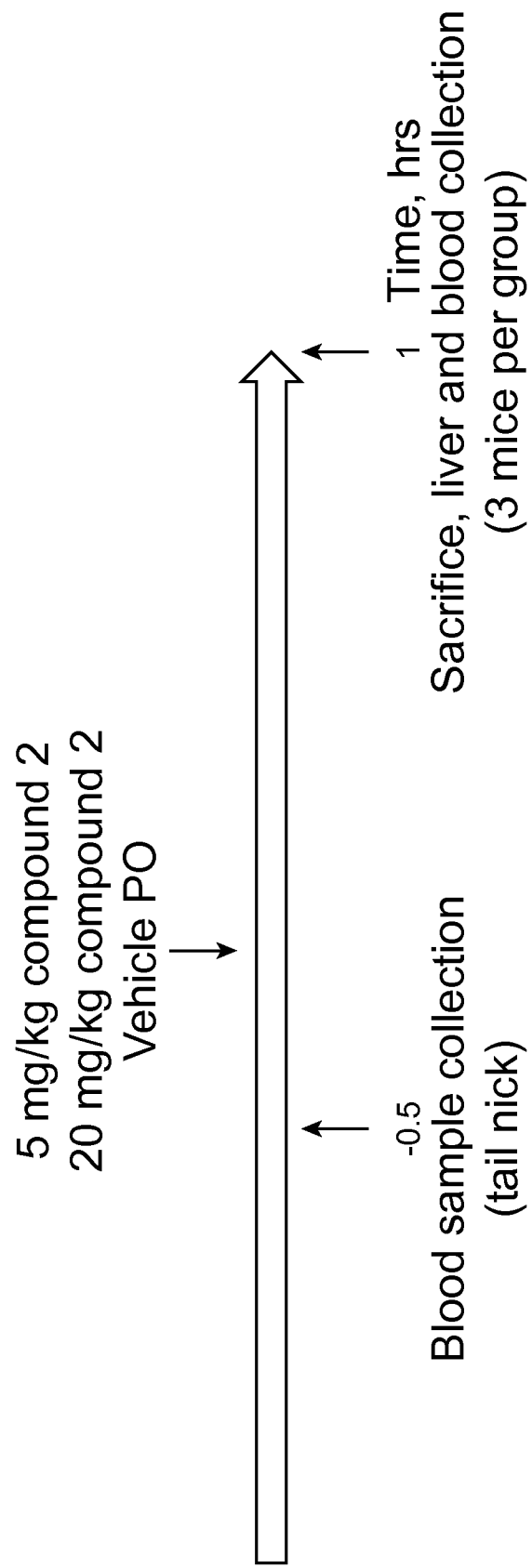
FIG. 12 is a schematic illustration of a single study in vivo.
Figure 13:
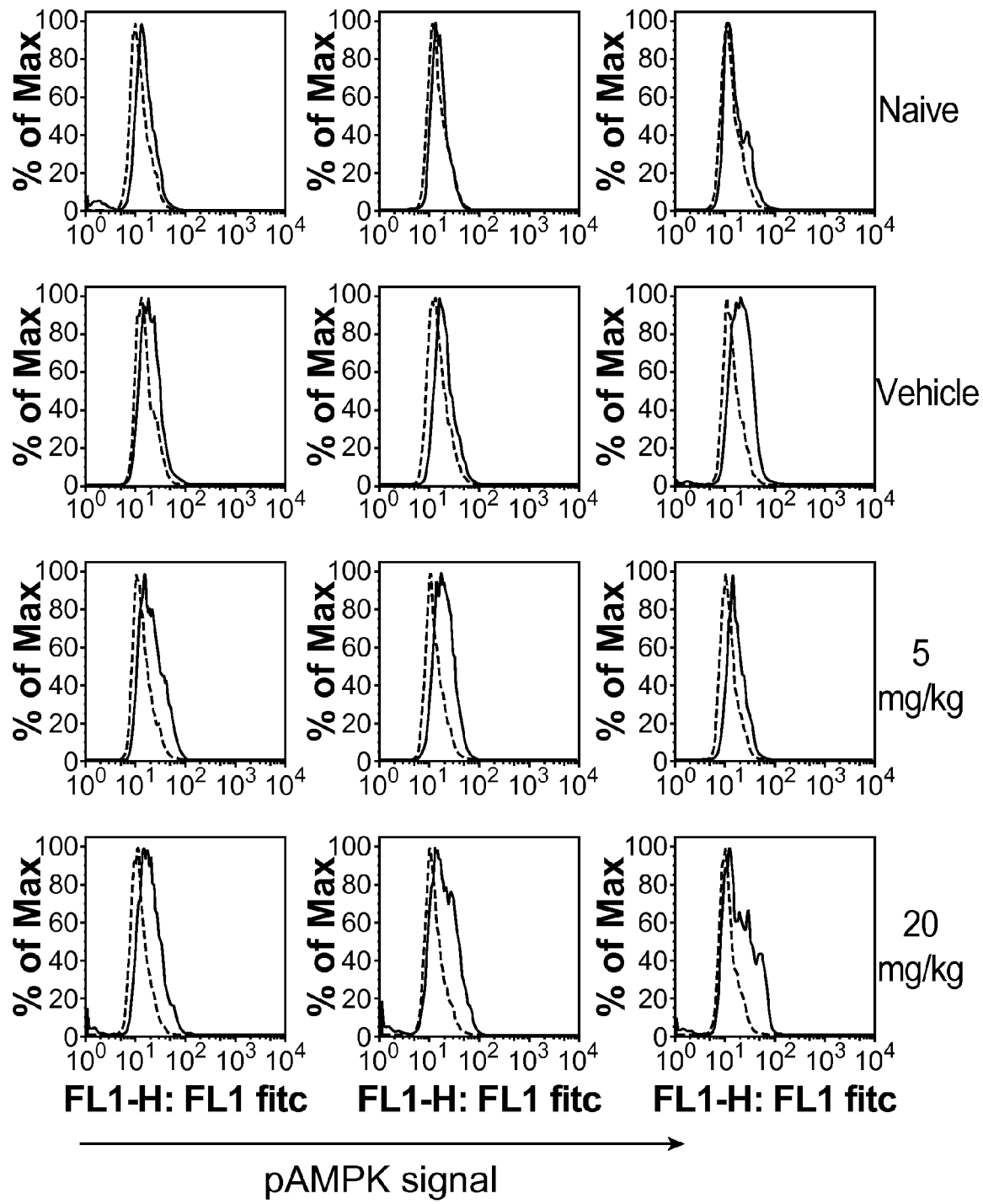
FIG. 13 is a series of graphs that show that AMPK phosphorylation after treatment by Compound 2, a known modulator of AMPK, is dose-dependent in mouse in vivo.

FIG. 11 shows an excellent linear correlation between pACC and pAMPK FACS EC50s in human whole blood (Y axis) for the tested compounds. ACC is a downstream target of AMPK, and AMPK is the only kinase to target inhibitory phosphorylation site on ACC.

pAMPK as a blood biomarker in vivo. FIG. 12 shows an outline of Compound 2's effect on AMPK activation in vivo study. FIG. 13 shows a one-dimension FACS plot of pAMPK staining in mouse blood after a single oral dose of Compound 2. Clear increase in pAMPK-positive population of cells is observed at the higher dose of Compound 2

Figure 14:
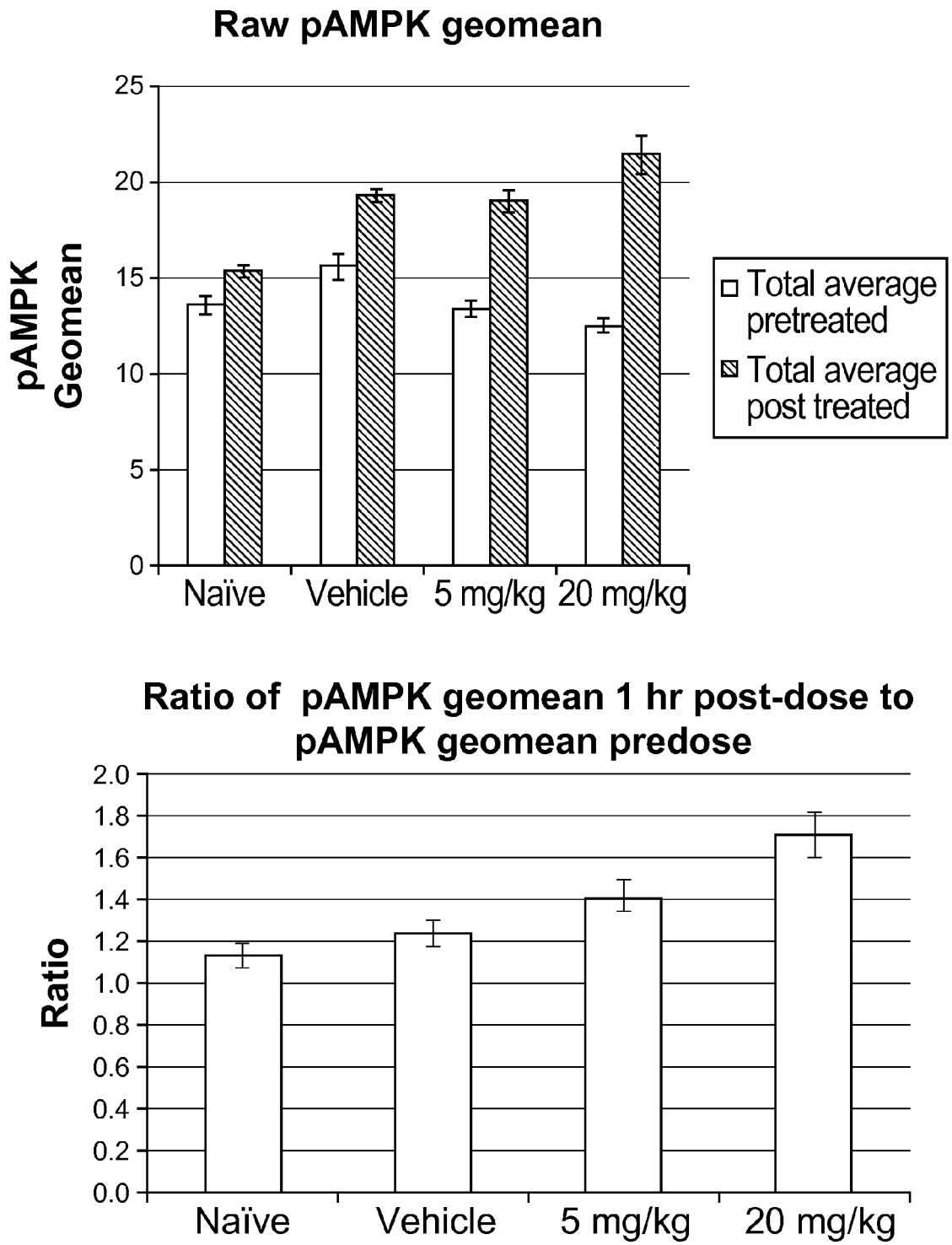
FIG. 14 shows two bar graphs showing that Compound 2, a known modulator of AMPK, increases AMPK phosphorylation in mouse blood lymphocytes

Example 15 pAMPK as a blood biomarker in vivo. Results are shown in FIG. 14. Top, geometric mean for pAMPK signal in blood-derived lymphocytes of mice treated with a single dose of Compound 2 at 5 and 20 mg/kg or with a vehicle control, as indicated. Measurements of pAMPK levels from blood samples taken prior to treatment are shown in blue and corresponding measurements taken 1 hr post-treatment are in red. Bottom, ratio of pAMPK signal geometric mean at 1 hr to that of 0.5 hrs prior to treatment for the same group of animals. Clear dose-dependent increase in signal is observed for blood samples from animals treated with Compound 2.

Example 16

Figure 15:
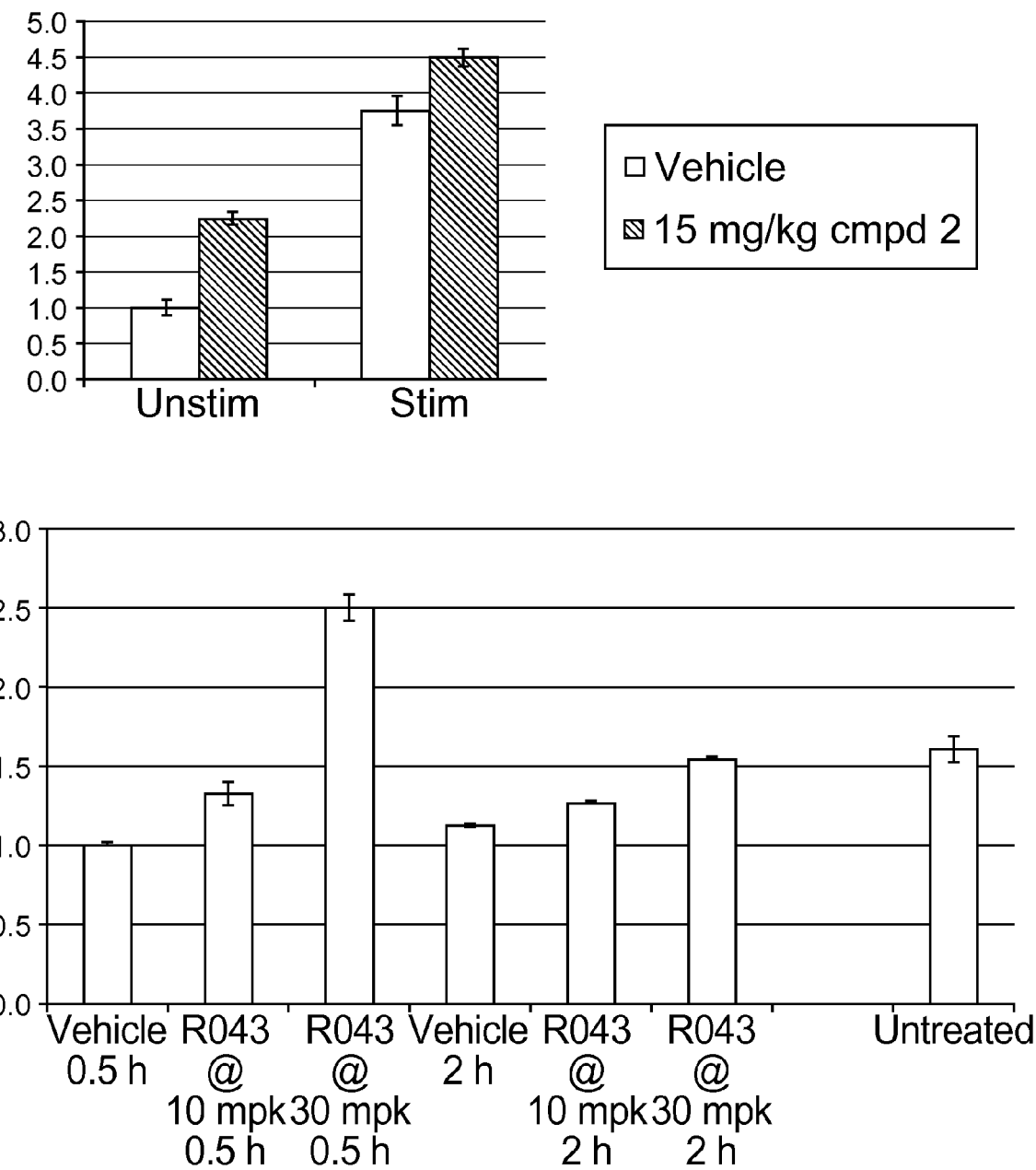
FIG. 15 shows bar graphs showing the results of a pAMPK FACS assay using spleen cells and compound 2.

FIG. 15 shows that a FACS-based pAMPK assay can be used to detect effects of the compounds on tissues other than blood. Spleens from the animals treated with Compound 2 (top) or R043 (bottom) were homogenized into single-cell suspension and the resulted samples were processed in the same way as blood and stained for pAMPK. Top, geometric mean for samples from vehicle- (right) or Compound 2-treated (left) animals, folds over vehicle control. Unstim, samples processed without any additional treatment. Stim, samples treated with 3.2 uM Compound 1 for 5 min at 37° C. before the processing to determine maximum AMPK stimulation level for cells in suspension.

Bottom, pAMPK geometric mean for spleen samples from animals treated with vehicle or Compound 3 at indicated doses and time points after oral dose, folds over vehicle control at 0.5 hr time point Conclusion: the same method can be use to assess pAMPK levels in solid tissues amendable to single-cell suspension processing, such as spleen and liver.

Example 17

Figure 16A:
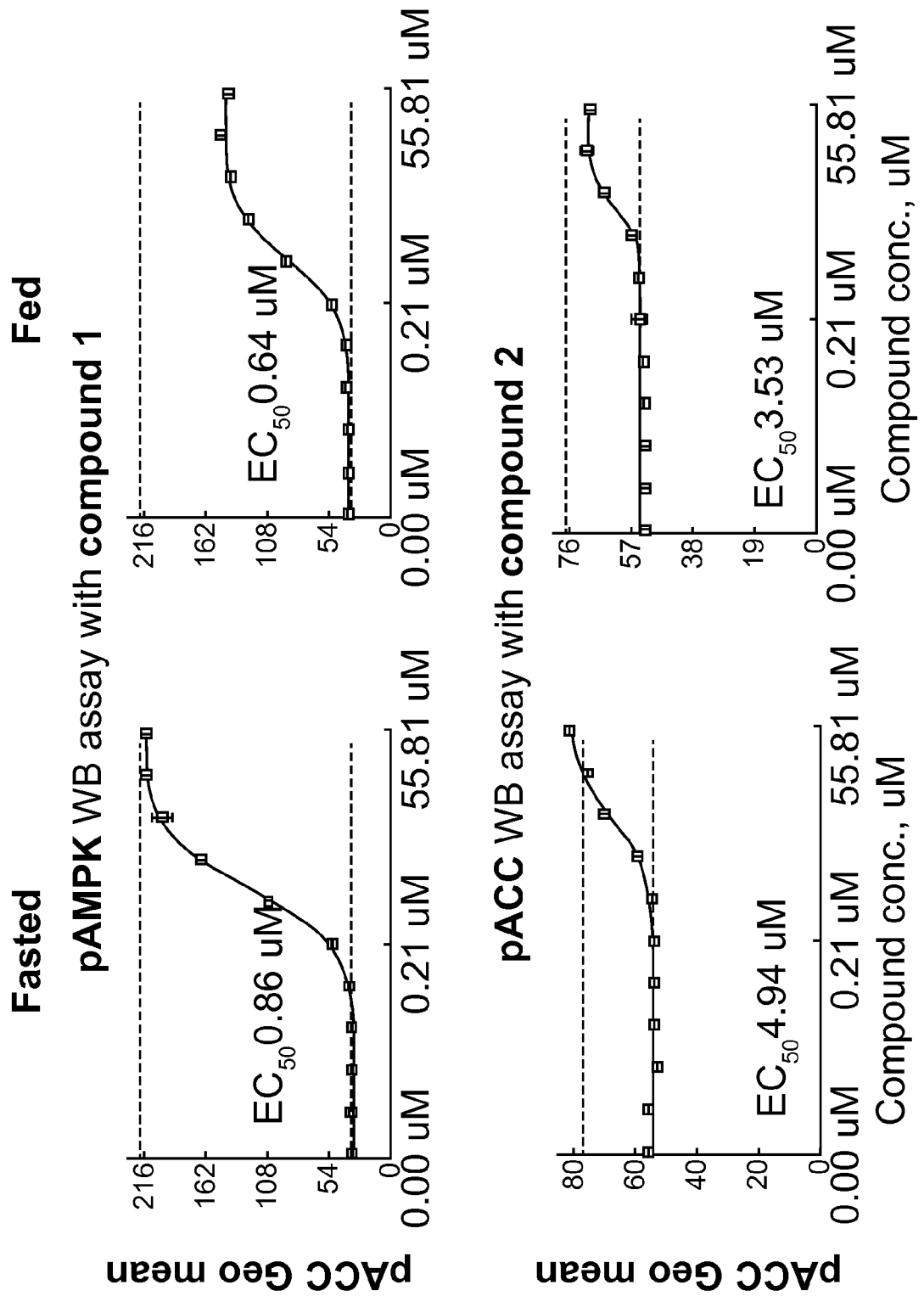
FIGS. 16A and 16B are panels of graphs that show that that maximum stimulation levels of pAMPK are significantly higher in fasted and lean mice compared to fed and obese mice, while unstimulated levels remain unchanged FIGS. 17A and 17B.
Figure 16B:
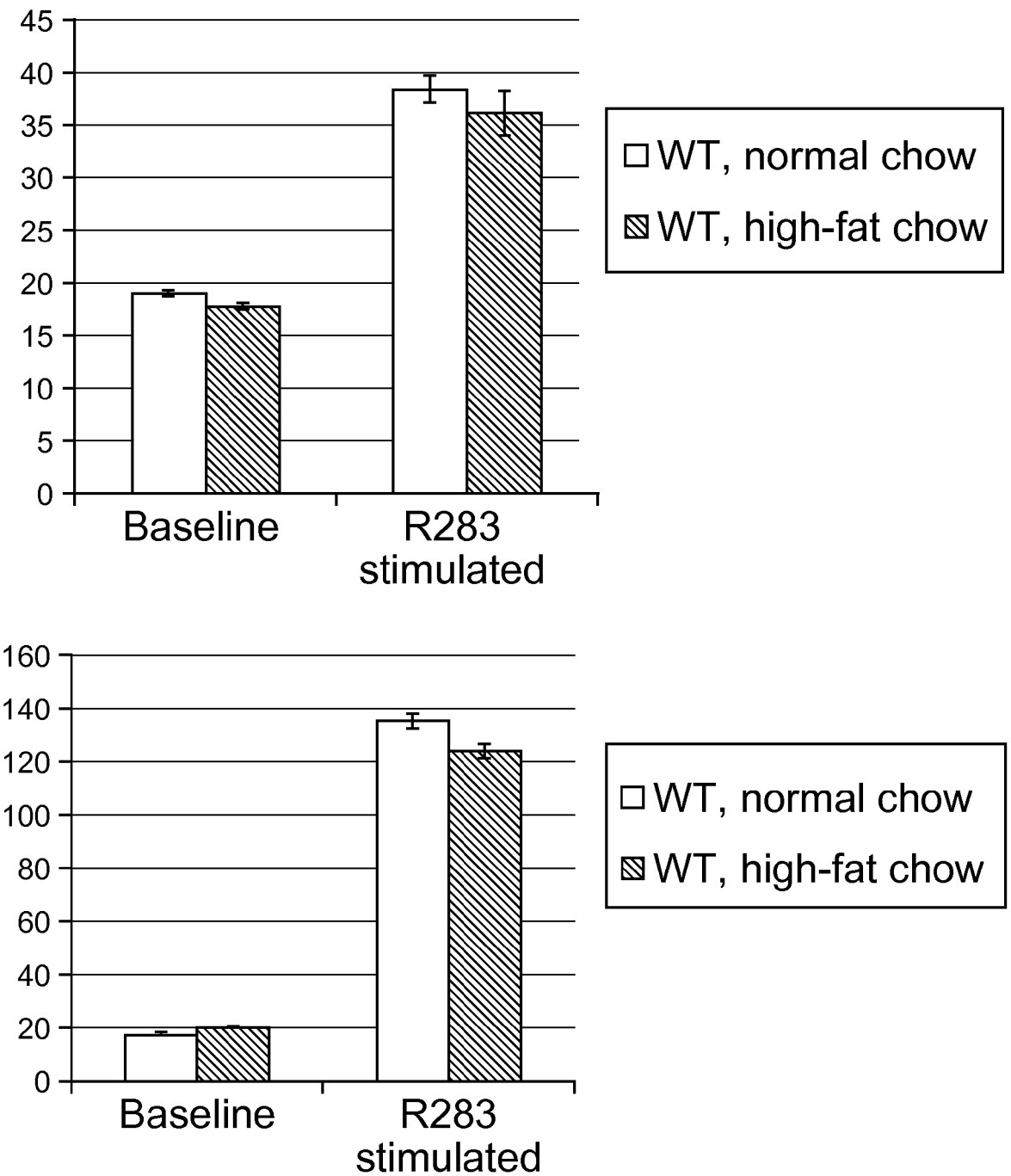

FIGS. 16A and 16B shows that maximum stimulation levels of pAMPK are significantly higher in fasted and lean mice compared to fed and obese mice, while unstimulated levels remain unchanged. FIG. 15 (top panel) shows that EC50 for any of the compounds tested did not depend on satiety. Baseline levels of both AMPK and ACC phosphorylation remained unchanged in both groups, while maximum stimulation levels for both were significantly higher in fasted group. FIG. 15 top panel shows the pAMPK levels in the blood of obese and lean mice before and after ex vivo stimulation with compound 1. The bottom panel of FIG. 15 shows pAMPK levels in the splenocytes of obese and lean mice before and after ex vivo stimulation with R283.

Figure 17A:
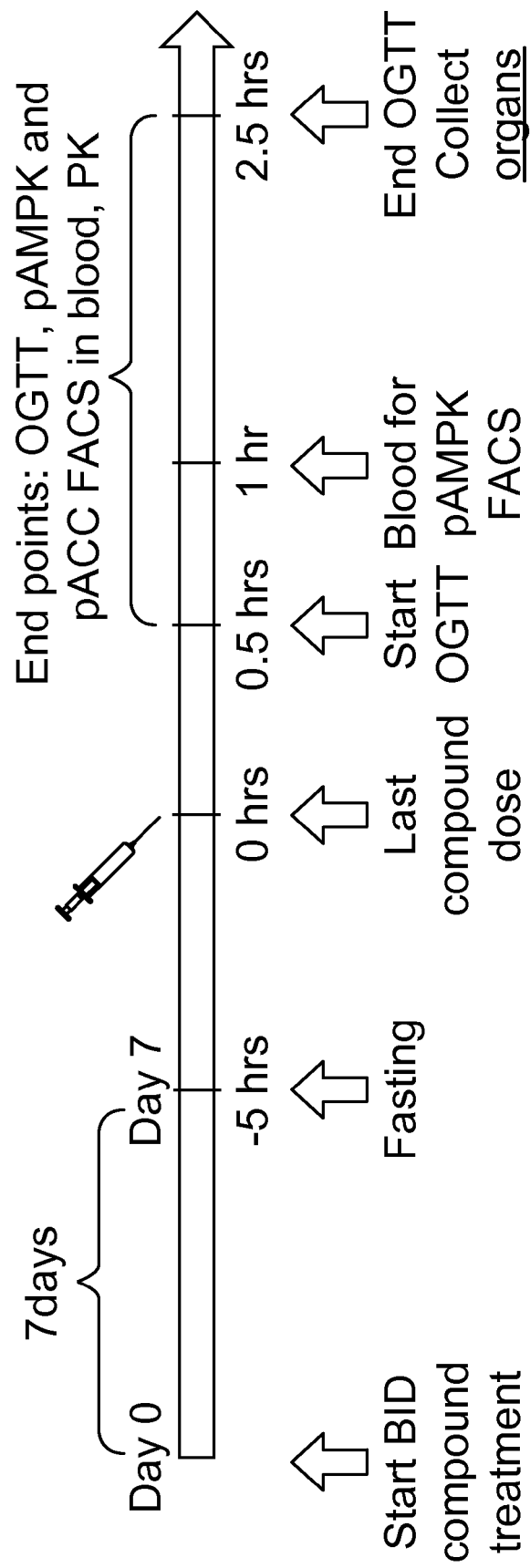
Figure 17B:
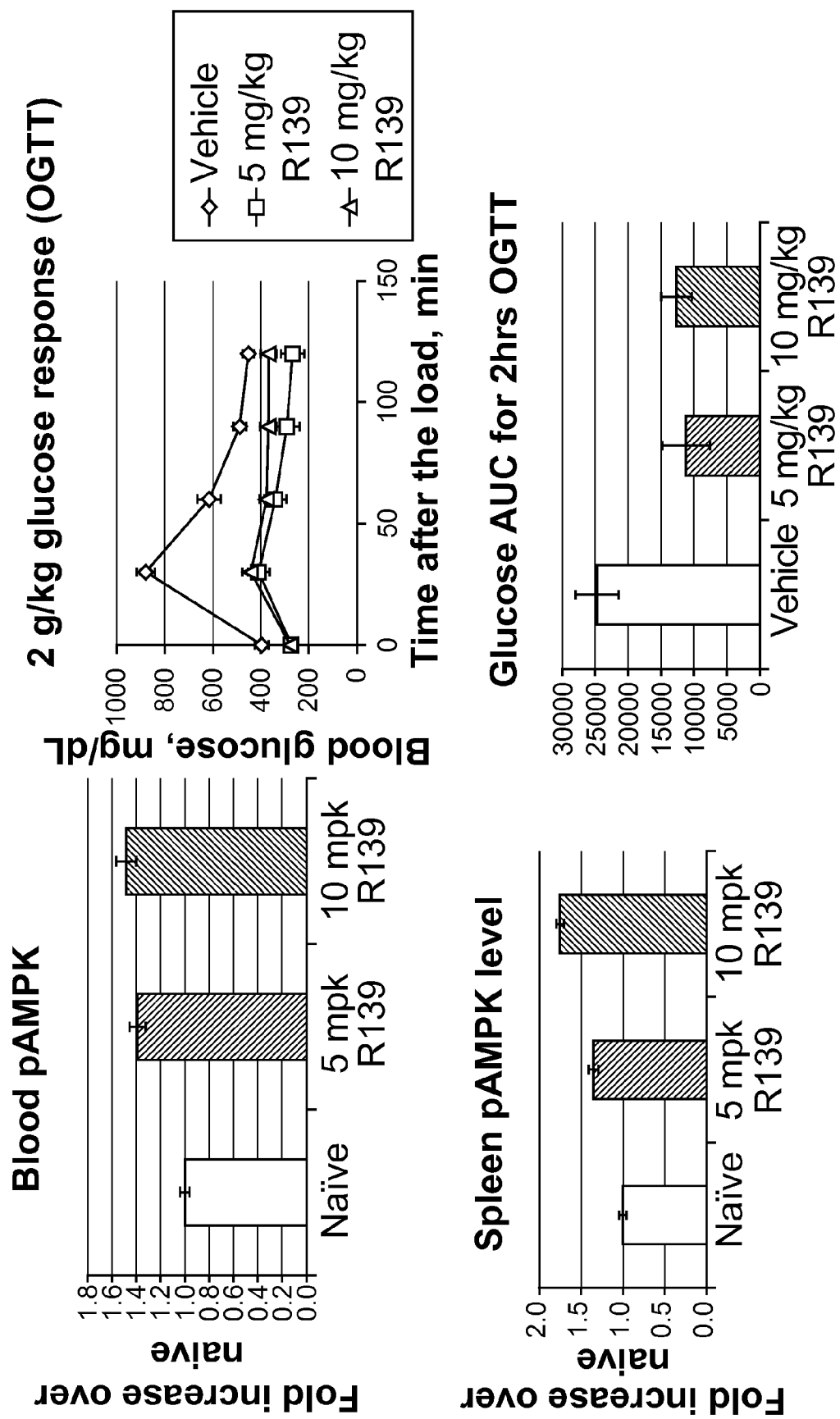
FIG. 17B shows that there is a reasonable correlation between OGTT and PK/PD results.

FIG. 17A shows an experimental plan and FIG. 17B shows that there is a reasonable correlation between OGTT and PK/PD results.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for determining the metabolic health of a subject, comprising:
    a) obtaining a blood sample from a subject and permeabilizing the cells of the blood sample;
    b) contacting the permeabilized cells of the blood sample with a fluorescently detectable antibody that specifically binds to phospho-adenosine monophosphate kinase (AMPK);
    c) measuring the amount of the fluorescently detectable antibody bound to phospho-AMPK in a plurality of the permeabilized cells in the blood sample, wherein the measuring comprises detecting the level of fluorescence signal on a single-cell basis, using flow cytometry; and
    d) calculating a geometric mean fluorescence value of the blood sample based on the measurements obtained in (c), wherein the geometric mean fluorescence value provides an indication of the level of AMPK activation in said plurality of permeabilized cells that correlates with the metabolic health of the subject.

2. The method of claim 1, wherein said plurality of permeabilized cells is a plurality of permeabilized white blood cells.

3. The method of claim 2, wherein said plurality of permeabilized cells is composed of a plurality of permeabilized lymphocytes or granulocytes.

4. The method of claim 2, wherein the calculating comprises calculating a geometric mean fluorescence value in a subset of the plurality of permeabilized cells.

5. The method of claim 4, wherein the subset of the plurality of permeabilized cells comprises lymphocytes or granulocytes.

6. The method of claim 1, wherein said method further comprises:
    prior to said contacting step: b), contacting blood with a first amount of a test agent ex vivo or in vivo; and
    comparing said geometric mean fluorescence value to a geometric mean fluorescence value obtained by the method of claim 1 from a reference sample of blood cells that is either not contacted with the test agent, or contacted with a second amount of the test agent wherein the first amount of the test agent and the second amount of the test agent are different, thereby determining a change in the level of AMPK activation in said plurality of permeabilized cells induced by the test agent.

7. The method of claim 6, wherein said contacting blood with a first amount of the test agent comprises administering said test agent to a subject and then drawing blood from said subject after a specified period of time.

8. The method of claim 6, wherein said contacting blood with a first amount of the test agent comprises drawing blood from a subject and then contacting said test agent with the drawn blood for a specified period of time.

9. The method of claim 6, wherein said test agent is known to change AMPK activation level.

10. The method of claim 6, wherein it is not known if said test agent induces a change in AMPK activation level.

11. The method of claim 6, wherein said reference sample comprises blood cells obtained from the same subject as said blood sample that is contacted with the test agent.

12. The method of claim 6, wherein said reference sample has not been contacted with said test agent.

13. The method of claim 6, wherein said blood sample is contacted with a first amount of said test agent and the reference sample is contacted with a second amount of said test agent, wherein the first amount and second amount are different.

14. A method of determining the effect of a change in lifestyle on AMPK activation in a subject, comprising:
   a) subjecting a subject to a change in lifestyle;
   b) obtaining a blood sample from said subject and permeablizing the cells of the blood sample;
   c) contacting the permeabilized cells of the blood sample with a fluorescently detectable antibody that specifically binds to phospho-adenosine monophosphate kinase (AMPK);
   d) measuring the amount of the fluorescently detectable antibody bound to phospho-AMPK in a plurality of permeabilized cells in the blood sample, wherein the measuring comprises detecting the level of fluorescence signal on a single-cell basis, using flow cytometry;
   e) calculating a geometric mean fluorescence value of the blood sample based on the measurements obtained in (d), wherein the geometric mean fluorescence value provides an indication of the level of AMPK activation in said plurality of permeabilized cells that correlates with the metabolic health of the subject; and
   f) comparing said level of AMPK activation to the level of AMPK activation obtained from a reference sample of blood cells from the subject before the change in lifestyle, thereby determining the effect of said change in lifestyle on AMPK activation of said subject.

15. The method of claim 14, wherein said change in lifestyle is a diet.

16. The method of claim 14, wherein said change in lifestyle is increased exercise.

\* \* \* \* \*